US009642644B2

(12) United States Patent
Houser et al.

(10) Patent No.: US 9,642,644 B2
(45) Date of Patent: May 9, 2017

(54) SURGICAL INSTRUMENTS

(71) Applicant: Ethicon Endo-Surgery, Inc., Cincinnati, OH (US)

(72) Inventors: Kevin L. Houser, Springboro, OH (US); Stephanie J. Muir, Loveland, OH (US); Louis T. DeLuca, Flower Mound, TX (US); Daniel W. Price, Loveland, OH (US); William D. Boyd, Mason, OH (US); Galen C. Robertson, Apex, NC (US); Michael J. O'Neil, West Barnstable, MA (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

(21) Appl. No.: 14/645,786

(22) Filed: Mar. 12, 2015

(65) Prior Publication Data

US 2015/0257781 A1 Sep. 17, 2015

Related U.S. Application Data

(62) Division of application No. 14/444,335, filed on Jul. 28, 2014, now Pat. No. 9,220,527, which is a division
(Continued)

(51) Int. Cl.
*A61B 17/32* (2006.01)
*A61L 2/07* (2006.01)
(Continued)

(52) U.S. Cl.
CPC .. *A61B 17/320092* (2013.01); *A61B 18/1442* (2013.01); *A61L 2/07* (2013.01);
(Continued)

(58) Field of Classification Search
CPC ...... A61B 17/32002; A61B 17/320092; A61B 18/1442; A61B 2017/00115;
(Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| AU | 2003241752 A1 | 9/2003 |
| CA | 2535467 A1 | 4/1993 |

(Continued)

OTHER PUBLICATIONS

Partial Supplementary European Search Report for 08782286.2, dated Apr. 1, 2015 (7 pages).
(Continued)

*Primary Examiner* — Ashley Fishback

(57) ABSTRACT

A surgical device. The surgical device may comprise a transducer configured to provide vibrations along a longitudinal axis and an end effector coupled to the transducer and extending from the transducer along the longitudinal axis. The surgical device also may comprise a lower jaw extending parallel to the end effector. The lower jaw may comprise a clamp face extending toward the longitudinal axis. Also, the lower jaw may be slidable relative to the end effector to bring the clamp face toward a distal end of the end effector.

20 Claims, 36 Drawing Sheets

Related U.S. Application Data of application No. 11/881,602, filed on Jul. 27, 2007, now Pat. No. 8,808,319.

(51) Int. Cl.
*A61L 2/08* (2006.01)
*A61L 2/20* (2006.01)
*A61B 18/14* (2006.01)
*A61N 7/00* (2006.01)
A61B 10/06 (2006.01)
A61B 17/3205 (2006.01)
A61B 17/29 (2006.01)
A61B 17/00 (2006.01)
A61B 18/00 (2006.01)

(52) U.S. Cl.
CPC .............. *A61L 2/081* (2013.01); *A61L 2/082* (2013.01); *A61L 2/087* (2013.01); *A61L 2/206* (2013.01); *A61N 7/00* (2013.01); A61B 10/06 (2013.01); A61B 17/32002 (2013.01); A61B 17/32053 (2013.01); A61B 2017/00128 (2013.01); A61B 2017/2944 (2013.01); A61B 2017/32004 (2013.01); A61B 2017/32008 (2013.01); A61B 2017/320008 (2013.01); A61B 2017/320064 (2013.01); A61B 2017/320072 (2013.01); A61B 2017/320076 (2013.01); A61B 2018/00589 (2013.01); A61B 2018/00601 (2013.01); A61B 2018/00607 (2013.01); A61B 2018/00642 (2013.01); A61B 2018/1452 (2013.01); A61B 2217/005 (2013.01); A61B 2560/02 (2013.01); Y10T 29/49716 (2015.01)

(58) Field of Classification Search
CPC .. A61B 2017/00128; A61B 2017/2944; A61B 2017/32004; A61B 2017/320064; A61B 2017/320072; A61B 2017/320076; A61B 2018/00589; A61B 2018/00601; A61B 2018/00607; A61B 2018/00636; A61B 2018/00642; A61B 2018/1452

See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,442,966 A | 6/1948 | Wallace |
| 2,597,564 A | 5/1952 | Bugg |
| 2,704,333 A | 3/1955 | Calosi et al. |
| 2,736,960 A | 3/1956 | Armstrong |
| 2,845,072 A | 7/1958 | Shafer |
| 2,849,788 A | 9/1958 | Creek |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,526,219 A | 9/1970 | Balamuth |
| 3,554,198 A | 1/1971 | Tatoian et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,808,154 A | 2/1989 | Freeman |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |

(56) References Cited

U.S. PATENT DOCUMENTS

| | | | |
|---|---|---|---|
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grezeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,312,023 A | 5/1994 | Green et al. |
| 5,312,425 A | 5/1994 | Evans et al. |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,553,675 A * | 9/1996 | Pitzen ............... A61B 17/1628 173/217 |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,618,304 A | 4/1997 | Hart et al. |
| 5,618,492 A | 4/1997 | Auten et al. |
| 5,620,447 A | 4/1997 | Smith et al. |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,717 A | 5/1997 | Yoon |
| 5,640,741 A | 6/1997 | Yano |
| D381,077 S | 7/1997 | Hunt |
| 5,651,780 A | 7/1997 | Jackson et al. |
| 5,653,713 A | 8/1997 | Michelson |
| 5,662,662 A | 9/1997 | Bishop et al. |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,700,261 A | 12/1997 | Brinkerhoff |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,797,959 A | 8/1998 | Castro et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |

(56) References Cited

U.S. PATENT DOCUMENTS

| | | | |
|---|---|---|---|
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,299,591 B1 | 10/2001 | Banko |
| 6,306,131 B1 | 10/2001 | Hareyama |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,538 B1 | 8/2002 | Blewett et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |

(56) References Cited

U.S. PATENT DOCUMENTS

| | | |
|---|---|---|
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,558,376 B2 | 5/2003 | Bishop |
| 6,561,983 B2 | 5/2003 | Cronin et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,716,215 B1 | 4/2004 | David et al. |
| 6,719,692 B2 | 4/2004 | Kleffner et al. |
| 6,719,776 B2 | 4/2004 | Baxter |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,618 B2 | 8/2006 | Couture |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |

(56) References Cited

U.S. PATENT DOCUMENTS

| | | |
|---|---|---|
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,244,262 B2 | 7/2007 | Wiener et al. |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |
| 7,300,446 B2 | 11/2007 | Beaupre |
| 7,303,531 B2 | 12/2007 | Lee et al. |
| 7,303,557 B2 | 12/2007 | Wham et al. |
| 7,306,597 B2 | 12/2007 | Manzo |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,364,577 B2 | 4/2008 | Wham et al. |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,544,200 B2 | 6/2009 | Houser |
| 7,549,564 B2 | 6/2009 | Boudreaux |
| 7,559,450 B2 | 7/2009 | Wales et al. |
| 7,567,012 B2 | 7/2009 | Namikawa |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,607,557 B2 | 10/2009 | Shelton, IV et al. |
| 7,621,930 B2 | 11/2009 | Houser |
| 7,641,653 B2 | 1/2010 | Dalla Betta et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| 7,721,935 B2 | 5/2010 | Racenet et al. |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |

(56) References Cited

U.S. PATENT DOCUMENTS

| | | |
|---|---|---|
| 7,775,972 B2 | 8/2010 | Brock et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,819,819 B2 | 10/2010 | Quick et al. |
| 7,821,143 B2 | 10/2010 | Wiener |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |
| 8,105,323 B2 | 1/2012 | Buysse et al. |
| 8,142,461 B2 | 3/2012 | Houser et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,502 B2 | 6/2012 | Smith et al. |
| 8,207,651 B2 | 6/2012 | Gilbert |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,241,271 B2 | 8/2012 | Millman et al. |
| 8,246,575 B2 | 8/2012 | Viola |
| 8,246,615 B2 | 8/2012 | Behnke |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,888 B2 | 10/2012 | Whitman |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,303,583 B2 | 11/2012 | Hosier et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,357,103 B2 | 1/2013 | Mark et al. |
| 8,366,727 B2 | 2/2013 | Witt et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,545 B2 | 4/2013 | Smith et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,460,288 B2 | 6/2013 | Tamai et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,359 B2 | 8/2013 | Whitman et al. |

(56) References Cited

U.S. PATENT DOCUMENTS

| | | | |
|---|---|---|---|
| 8,512,365 B2 | 8/2013 | Wiener et al. |
| 8,523,889 B2 | 9/2013 | Stulen et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,709,031 B2 | 4/2014 | Stulen |
| 8,747,351 B2 | 6/2014 | Schultz |
| 8,749,116 B2 | 6/2014 | Messerly et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,764,735 B2 | 7/2014 | Coe et al. |
| 8,773,001 B2 | 7/2014 | Wiener et al. |
| 8,779,648 B2 | 7/2014 | Giordano et al. |
| 8,784,418 B2 | 7/2014 | Romero |
| 8,808,319 B2 | 8/2014 | Houser et al. |
| 8,827,992 B2 | 9/2014 | Koss et al. |
| 8,845,537 B2 | 9/2014 | Tanaka et al. |
| 8,882,791 B2 | 11/2014 | Stulen |
| 8,888,776 B2 | 11/2014 | Dietz et al. |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,911,460 B2 | 12/2014 | Neurohr et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,547 B2 | 2/2015 | Dietz et al. |
| 8,968,355 B2 | 3/2015 | Malkowski et al. |
| 8,974,477 B2 | 3/2015 | Yamada |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 9,017,326 B2 | 4/2015 | DiNardo et al. |
| 9,039,695 B2 | 5/2015 | Giordano et al. |
| 9,044,261 B2 | 6/2015 | Houser |
| 9,050,093 B2 | 6/2015 | Aldridge et al. |
| 9,050,124 B2 | 6/2015 | Houser |
| 9,060,775 B2 | 6/2015 | Wiener et al. |
| 9,060,776 B2 | 6/2015 | Yates et al. |
| 9,066,747 B2 | 6/2015 | Robertson |
| 9,072,539 B2 | 7/2015 | Messerly et al. |
| 9,089,360 B2 | 7/2015 | Messerly et al. |
| 9,095,367 B2 | 8/2015 | Olson et al. |
| 9,107,689 B2 | 8/2015 | Robertson et al. |
| 9,113,940 B2 | 8/2015 | Twomey |
| 9,168,054 B2 | 10/2015 | Turner et al. |
| 9,198,714 B2 | 12/2015 | Worrell et al. |
| 9,220,527 B2 | 12/2015 | Houser et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,921 B2 | 1/2016 | Messerly et al. |
| 9,241,728 B2 | 1/2016 | Price et al. |
| 9,241,731 B2 | 1/2016 | Boudreaux et al. |
| 9,259,234 B2 | 2/2016 | Robertson et al. |
| 9,283,045 B2 | 3/2016 | Rhee et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055417 A1* | 3/2003 | Truckai .......... A61B 17/320092 606/27 |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |

(56) References Cited

U.S. PATENT DOCUMENTS

| | | |
|---|---|---|
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0271030 A1 | 11/2006 | Francis et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0175959 A1* | 8/2007 | Shelton, IV ..... A61B 17/07207 227/178.1 |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2007/0288055 A1 | 12/2007 | Lee |
| 2008/0009848 A1 | 1/2008 | Paraschiv et al. |
| 2008/0013809 A1 | 1/2008 | Zhu et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1* | 4/2008 | Blier ............. A61B 17/320068 606/169 |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0088785 A1 | 4/2009 | Masuda |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0163807 A1 | 6/2009 | Sliwa |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0077648 A1 | 3/2011 | Lee et al. |
| 2011/0087218 A1 | 4/2011 | Boudreaux et al. |
| 2011/0112526 A1 | 5/2011 | Fritz et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0290853 A1 | 12/2011 | Shelton, IV et al. |
| 2011/0290856 A1 | 12/2011 | Shelton, IV et al. |

(56) References Cited

U.S. PATENT DOCUMENTS

| | | |
|---|---|---|
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0022583 A1 | 1/2012 | Sugalski et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0101495 A1 | 4/2012 | Young et al. |
| 2012/0101501 A1 | 4/2012 | Nishimura et al. |
| 2012/0109159 A1 | 5/2012 | Jordan et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0269676 A1 | 10/2012 | Houser et al. |
| 2012/0330307 A1 | 12/2012 | Ladtkow et al. |
| 2013/0012957 A1 | 1/2013 | Shelton, IV et al. |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0245659 A1 | 9/2013 | Robertson et al. |
| 2013/0253498 A1 | 9/2013 | Germain et al. |
| 2013/0267975 A1 | 10/2013 | Timm et al. |
| 2013/0274734 A1 | 10/2013 | Maass et al. |
| 2013/0282038 A1 | 10/2013 | Dannaher et al. |
| 2013/0282039 A1 | 10/2013 | Wiener et al. |
| 2013/0296908 A1 | 11/2013 | Schulte et al. |
| 2013/0338661 A1 | 12/2013 | Behnke, II |
| 2013/0345689 A1 | 12/2013 | Ruddenklau et al. |
| 2014/0005640 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276970 A1 | 9/2014 | Messerly et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |
| 2015/0250495 A1 | 9/2015 | Robertson et al. |
| 2015/0257780 A1 | 9/2015 | Houser |
| 2015/0265308 A1 | 9/2015 | Houser et al. |
| 2015/0282834 A1 | 10/2015 | Robertson |
| 2015/0327883 A1 | 11/2015 | Messerly et al. |
| 2015/0328484 A1 | 11/2015 | Messerly et al. |
| 2015/0340586 A1 | 11/2015 | Wiener et al. |
| 2015/0351789 A1 | 12/2015 | Robertson et al. |
| 2016/0030076 A1 | 2/2016 | Faller et al. |
| 2016/0089209 A1 | 3/2016 | Parihar et al. |
| 2016/0089533 A1 | 3/2016 | Turner et al. |
| 2016/0095617 A1 | 4/2016 | Price et al. |

FOREIGN PATENT DOCUMENTS

| | | |
|---|---|---|
| CN | 1233944 A | 11/1999 |
| CN | 1253485 A | 5/2000 |
| CN | 1634601 A | 7/2005 |
| CN | 1640365 A | 7/2005 |
| CN | 1694649 A | 11/2005 |
| CN | 1922563 A | 2/2007 |
| CN | 1951333 A | 4/2007 |
| CN | 101040799 A | 9/2007 |
| CN | 101467917 A | 1/2009 |
| DE | 3904558 A1 | 8/1990 |
| DE | 9210327 U1 | 11/1992 |
| DE | 4323585 A1 | 1/1995 |
| DE | 19608716 C1 | 4/1997 |
| DE | 20021619 U1 | 3/2001 |
| DE | 10042606 A1 | 8/2001 |
| EP | 0136855 B1 | 9/1984 |
| EP | 0171967 A2 | 2/1986 |
| EP | 1839599 A1 | 10/1987 |
| EP | 0336742 A2 | 4/1989 |
| EP | 0342448 A1 | 11/1989 |
| EP | 0424685 B1 | 5/1991 |
| EP | 0443256 A1 | 8/1991 |

(56) References Cited

FOREIGN PATENT DOCUMENTS

| | | |
|---|---|---|
| EP | 0456470 A1 | 11/1991 |
| EP | 0598976 A2 | 1/1994 |
| EP | 0677275 A2 | 3/1995 |
| EP | 0482195 B1 | 1/1996 |
| EP | 0695535 A1 | 2/1996 |
| EP | 0741996 A2 | 11/1996 |
| EP | 0612570 B1 | 6/1997 |
| EP | 1108394 A2 | 6/2001 |
| EP | 1138264 A1 | 10/2001 |
| EP | 0908148 B1 | 1/2002 |
| EP | 1229515 A2 | 8/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1433425 B1 | 6/2006 |
| EP | 1256323 B1 | 9/2006 |
| EP | 1698289 A2 | 9/2006 |
| EP | 1704824 A1 | 9/2006 |
| EP | 1749479 A1 | 2/2007 |
| EP | 1815950 A1 | 8/2007 |
| EP | 1844720 A1 | 10/2007 |
| EP | 1862133 A1 | 12/2007 |
| EP | 1875875 A1 | 1/2008 |
| EP | 1199045 B1 | 6/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1997438 A2 | 12/2008 |
| EP | 1477104 B1 | 1/2009 |
| EP | 2014218 A2 | 1/2009 |
| EP | 2042112 A2 | 4/2009 |
| EP | 1832259 B1 | 6/2009 |
| EP | 2074959 A1 | 7/2009 |
| EP | 2106758 A1 | 10/2009 |
| EP | 2111813 A1 | 10/2009 |
| EP | 2200145 A1 | 6/2010 |
| EP | 1214913 B1 | 7/2010 |
| EP | 2238938 A1 | 10/2010 |
| EP | 2298154 A2 | 3/2011 |
| EP | 1510178 B1 | 6/2011 |
| EP | 2305144 A1 | 6/2011 |
| EP | 2335630 A1 | 6/2011 |
| EP | 1502551 B1 | 7/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2510891 A1 | 10/2012 |
| EP | 2316359 B1 | 3/2013 |
| EP | 1586275 B1 | 5/2013 |
| EP | 1616529 B1 | 9/2013 |
| EP | 2583633 B1 | 10/2014 |
| GB | 1482943 A | 8/1977 |
| GB | 2032221 A | 4/1980 |
| GB | 2317566 A | 4/1998 |
| GB | 2379878 B | 11/2004 |
| GB | 2447767 B | 8/2011 |
| JP | S 50-100891 | 12/1973 |
| JP | S 59-68513 | 10/1982 |
| JP | S 59141938 A | 8/1984 |
| JP | 62-221343 A | 9/1987 |
| JP | S 62-227343 | 10/1987 |
| JP | 62-292153 A | 12/1987 |
| JP | S 62-292154 A | 12/1987 |
| JP | 63-109386 A | 5/1988 |
| JP | 63-315049 A | 12/1988 |
| JP | H 01-151452 | 6/1989 |
| JP | H 01-198540 A | 8/1989 |
| JP | 02-71510 U | 5/1990 |
| JP | 2-286149 A | 11/1990 |
| JP | H 02-292193 A | 12/1990 |
| JP | H 03-37061 A | 2/1991 |
| JP | 04-25707 U | 2/1992 |
| JP | H 04-64351 A | 2/1992 |
| JP | 4-30508 U | 3/1992 |
| JP | H 04-150847 A | 5/1992 |
| JP | H 04-152942 A | 5/1992 |
| JP | 05-095955 A | 4/1993 |
| JP | H 05-115490 A | 5/1993 |
| JP | H 06-070938 A | 3/1994 |
| JP | 6-104503 A | 4/1994 |
| JP | 6-507081 A | 8/1994 |
| JP | H 06-217988 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 08-299351 A | 11/1996 |
| JP | H 08-336545 A | 12/1996 |
| JP | H 09-503146 A | 3/1997 |
| JP | H 09-135553 A | 5/1997 |
| JP | H 09-140722 A | 6/1997 |
| JP | H 10-005237 A | 1/1998 |
| JP | 10-295700 A | 11/1998 |
| JP | H 11-501543 A | 2/1999 |
| JP | H 11-128238 | 5/1999 |
| JP | H 11-192235 A | 7/1999 |
| JP | 11-253451 A | 9/1999 |
| JP | H 11-318918 A | 11/1999 |
| JP | 2000-041991 A | 2/2000 |
| JP | 2000-070279 A | 3/2000 |
| JP | 2000-210299 A | 8/2000 |
| JP | 2000-287987 A | 10/2000 |
| JP | 2001-029353 A | 2/2001 |
| JP | 2001-502216 A | 2/2001 |
| JP | 2003612 A | 6/2001 |
| JP | 2001-309925 A | 11/2001 |
| JP | 2002-186901 A | 7/2002 |
| JP | 2002-204808 A | 7/2002 |
| JP | 2002-263579 A | 9/2002 |
| JP | 2002-301086 A | 10/2002 |
| JP | 2002-330977 A | 11/2002 |
| JP | 2002-542690 A | 12/2002 |
| JP | 2003-000612 A | 1/2003 |
| JP | 2003-010201 | 1/2003 |
| JP | 2003-510158 A | 3/2003 |
| JP | 2003-116870 A | 4/2003 |
| JP | 2003-126104 A | 5/2003 |
| JP | 2003-126110 A | 5/2003 |
| JP | 2003-310627 A | 5/2003 |
| JP | 2003-530921 A | 10/2003 |
| JP | 2003-339730 A | 12/2003 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-534451 A | 11/2005 |
| JP | 2006-6410 A | 1/2006 |
| JP | 2006-512149 A | 4/2006 |
| JP | 2006-116194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007-050181 A | 3/2007 |
| JP | 2007-229454 A | 9/2007 |
| JP | 2007-527747 A | 10/2007 |
| JP | 2008-508065 A | 3/2008 |
| JP | 2008-119250 A | 5/2008 |
| JP | 2008-521503 A | 6/2008 |
| JP | 2008-212679 A | 9/2008 |
| JP | 2008-536562 A | 9/2008 |

(56) References Cited

FOREIGN PATENT DOCUMENTS

| | | |
|---|---|---|
| JP | 2008-284374 | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-236177 A | 10/2009 |
| JP | 2009-254819 A | 11/2009 |
| JP | 2010-000336 A | 1/2010 |
| JP | 2010-514923 A | 5/2010 |
| JP | 2010-534522 A | 11/2010 |
| JP | 2010-540186 A | 12/2010 |
| JP | 2011-505198 A | 2/2011 |
| JP | 2012-235658 A | 11/2012 |
| JP | 5208761 B2 | 6/2013 |
| JP | D1339835 | 8/2015 |
| RU | 2154437 C1 | 8/2000 |
| RU | 22035 U1 | 3/2002 |
| WO | WO 92/22259 A2 | 12/1992 |
| WO | WO 93/08757 A1 | 5/1993 |
| WO | WO 93/14708 A1 | 8/1993 |
| WO | WO 93/16646 A1 | 9/1993 |
| WO | WO 93/20877 A1 | 10/1993 |
| WO | WO 94/21183 A1 | 9/1994 |
| WO | WO 94/24949 A1 | 11/1994 |
| WO | WO 95/09572 A1 | 4/1995 |
| WO | WO 95/34259 A1 | 12/1995 |
| WO | WO 96/30885 A1 | 10/1996 |
| WO | WO 96/39086 A1 | 12/1996 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 98/47436 A1 | 10/1998 |
| WO | WO 99/20213 A1 | 4/1999 |
| WO | WO 99/52489 A1 | 10/1999 |
| WO | WO 00/64358 A2 | 11/2000 |
| WO | WO 00/74585 A2 | 12/2000 |
| WO | WO 01/24713 A1 | 4/2001 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/098426 A1 | 11/2004 |
| WO | WO 2004/112618 A2 | 12/2004 |
| WO | WO 2005/117735 A1 | 12/2005 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/101661 A2 | 9/2006 |
| WO | WO 2006/119139 A2 | 11/2006 |
| WO | WO 2006/119376 A2 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/038538 A1 | 4/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/010565 A1 | 1/2009 |
| WO | WO 2009/018067 A1 | 2/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/073402 A2 | 6/2009 |
| WO | WO 2009/120992 A2 | 10/2009 |
| WO | WO 2010/017149 A1 | 2/2010 |
| WO | WO 2010/068783 A1 | 6/2010 |
| WO | WO 2011/008672 A2 | 1/2011 |
| WO | WO 2011/052939 A2 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 A1 | 9/2012 |
| WO | WO 2012/135705 A1 | 10/2012 |
| WO | WO 2012/135721 A1 | 10/2012 |
| WO | WO 2013/018934 A1 | 2/2013 |
| WO | WO 2013/062978 A2 | 5/2013 |

OTHER PUBLICATIONS

Extended European Search Report for 08782286.2, dated Jul. 17, 2015 (10 pages).
International Preliminary Report on Patentability for PCT/US2008/070964, Feb. 2, 2010 (10 pages).
International Search Report for PCT/US2008/070964, Dec. 15, 2008 (6 pages).
Technology Overview, printed from www.harmonicscalpel.com, internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., "Fundamentals of Heat and Mass Transfer", Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).

(56) References Cited

OTHER PUBLICATIONS

Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
http://www.apicalinstr.com/generators.htm.
http://www.dotmed.com/listing/electrosurical-unit/ethicon/ultracision-g110-/1466724.
http:/www.ethicon.com/gb-en/healthcare-professionals/products/energy-devices/capital//ge . . . .
http://www.4-traders.com/JOHNSON-JOHNSON-4832/news/Johnson-Johnson-Ethicon-E . . . .
http://www.medicalexpo.com/medical-manufacturer/electrosurgical-generator-6951.html.
http://www_megadyne.com/es_generator.php.
http://www.valleylab.com/product/es/generators/index.html.
Covidien 501(k) Summary Sonicision, dated Feb. 24, 2011 (7 pages).
Gerhard, Glen C., "Surgical Electrotechnology: Quo Vadis?," Biomedical Engineering, IEEE Transactions on , vol. BME-31, No. 12, pp. 787, 792, Dec. 1984.
Fowler, K.R., "A programmable, arbitrary waveform electrosurgical device," Engineering in Medicine and Biology Society, 1988. Proceedings of the Annual International Conference of the IEEE, vol., No., pp. 1324, 1325 vol. 3, Nov. 4-7, 1988.
LaCourse, Jr.; Vogt, M.C.; Miller, W.T., III; Selikowitz, S.M., "Spectral analysis interpretation of electro-surgical generator nerve and muscle stimulation," Biomedical Engineering, IEEE Transactions on , vol. 35, No. 7, pp. 505, 509, Jul. 1988.
U.S. Appl. No. 13/751,680, filed Jan. 28, 2013.

\* cited by examiner

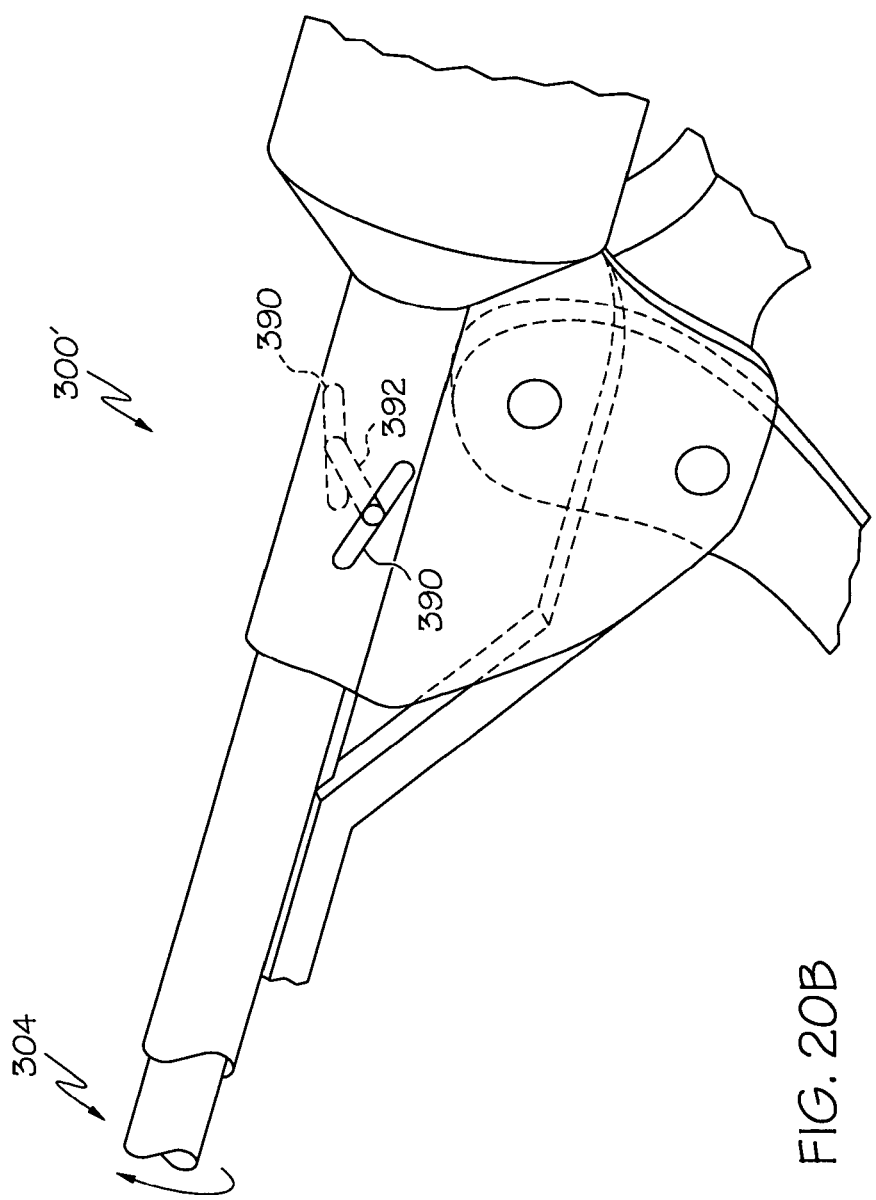

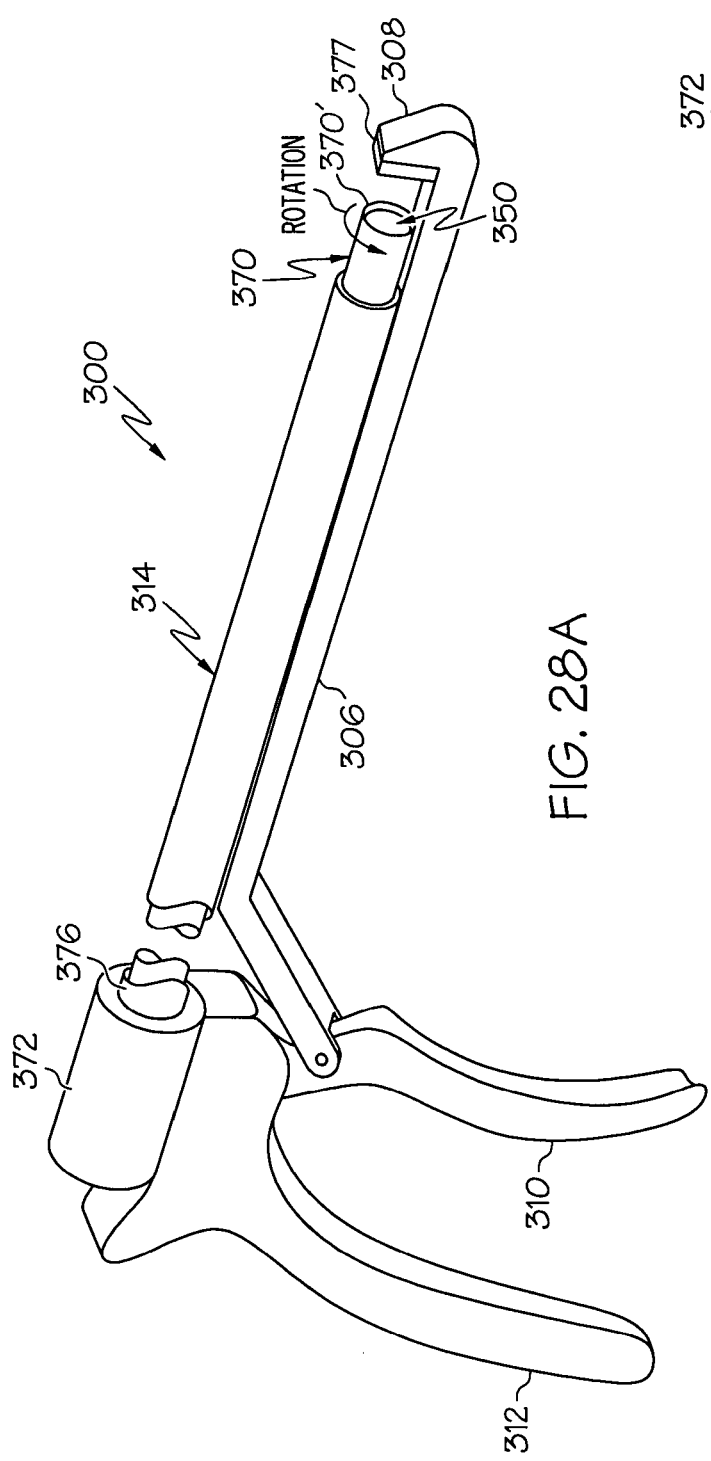
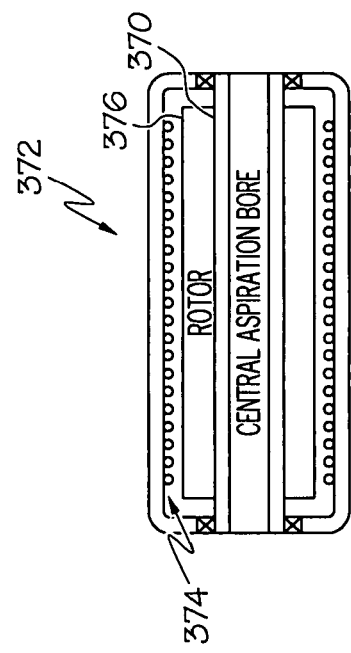
FIG. 28A
FIG. 28B

SURGICAL INSTRUMENTS

PRIORITY CLAIM

The present application is a divisional of U.S. patent application Ser. No. 14/444,335, filed on Jul. 28, 2014, which is incorporated by reference herein in its entirety and is a divisional of U.S. application Ser. No. 11/881,602, now issued as U.S. Pat. No. 8,808,319, filed on Jul. 27, 2007, which is incorporated herein by reference in its entirety.

BACKGROUND

Ultrasonic instruments, including both hollow core and solid core instruments, are used for the safe and effective treatment of many medical conditions. Ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue off bone. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end effector may be designed to perform numerous functions, including, for example, cutting and coagulation.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. Therefore, when an end effector is attached to a transducer the overall system frequency is the same frequency as the transducer itself.

The zero to peak amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.
The longitudinal excursion is defined as the peak-to-peak (p-t-p) amplitude, which is just twice the amplitude of the sine wave or 2A.

Ultrasonic surgical instruments may be divided into two types, single element end effector devices and multiple-element end effector devices. Single element end effector devices include instruments such as scalpels and ball coagulators. Single-element end effector instruments have limited ability to apply blade-to-tissue pressure when the tissue is soft and loosely supported. Sometimes, substantial pressure may be necessary to effectively couple ultrasonic energy to the tissue. This inability to grasp the tissue results in a further inability to fully coapt tissue surfaces while applying ultrasonic energy, leading to less-than-desired hemostasis and tissue joining. In these cases, multiple-element end effectors may be used. Multiple-element end effector devices, such as clamping coagulators, include a mechanism to press tissue against an ultrasonic blade that can overcome these deficiencies.

Many surgical procedures utilizing harmonic and non-harmonic instruments create extraneous tissue fragments and other materials at the surgical site. If this material is not removed, it may obstruct the clinician's view and also may interfere with the blade or other end effector of the surgical device. To remove the material, the clinician must remove the instrument from the surgical area and introduce an aspiration tool. This can break the clinician's concentration and also contribute to physical and mental fatigue.

Also, in some surgical procedures, it is desirable to remove a core or other integral portion of tissue. In these procedures, the clinician uses a first instrument to grasp and sometimes cut an outline of the tissue to be removed. Then a second instrument is utilized to remove the tissue from surrounding material, often while the tissue is still grasped by the first instrument. This process may be particularly challenging for clinicians because it can require the use of multiple instruments, often simultaneously. Also, many coring procedures are performed at very delicate portions of the anatomy that require precise cuts.

In addition, existing harmonic instruments allow the clinician to turn them on or off, but provide limited control over the power delivered to tissue once the instrument is turned on. This limits the usefulness of harmonic instruments in delicate surgical procedures, where fine cutting control is required.

SUMMARY

In one general aspect, the various embodiments are directed to a surgical device. The surgical device may comprise a transducer configured to provide vibrations along a longitudinal axis and an end effector coupled to the transducer and extending from the transducer along the longitudinal axis. The surgical device also may comprise a lower jaw extending parallel to the end effector. The lower jaw may comprise a clamp face extending toward the longitudinal axis. Also, the lower jaw may be slidable relative to the end effector to bring the clamp face toward a distal end of the end effector.

In another general aspect, the various embodiments are directed to another surgical device comprising an end effector. The end effector may comprise a hollow portion defining a central lumen and at least one member extended across at least a portion of the central lumen at about a distal end of the end effector.

In yet another general aspect, the various embodiments are directed to a surgical device comprising a central instrument and an outer sheath surrounding the central instrument. The central instrument may be configured to engage tissue, and may be slidable relative to the outer sheath. The outer sheath may comprise a distal edge configured to clamp the tissue when the central instrument is slid to a position proximal from the distal edge of the outer sheath.

According to still another general aspect, the various embodiments are directed to a surgical device comprising a transducer configured to energize an end effector and a trigger actuable to cause the end effector to be energized. The end effector may be coupled to the transducer. The surgical device may further comprise a sensor positioned to sense a force exerted on the trigger, and control circuit in communication with the sensor. The control circuit may be configured to increase power delivered to the end effector by the transducer in response to an increase of the force exerted on the trigger.

FIGURES

The novel features of the various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 4 illustrates one embodiment of a clamping mechanism that may be used with the surgical instrument shown in FIG. 1;

FIG. 20B illustrates one embodiment of the surgical device shown in FIG. 20A where the end effector is configured to rotate as it moves forward toward the clamp face;

FIG. 28A illustrates one embodiment of the surgical device of FIG. 10 including a rotating end effector;

FIG. 28B illustrates one embodiment of an electric motor for use with the surgical device of FIG. 28A.

DESCRIPTION

Figure 1:
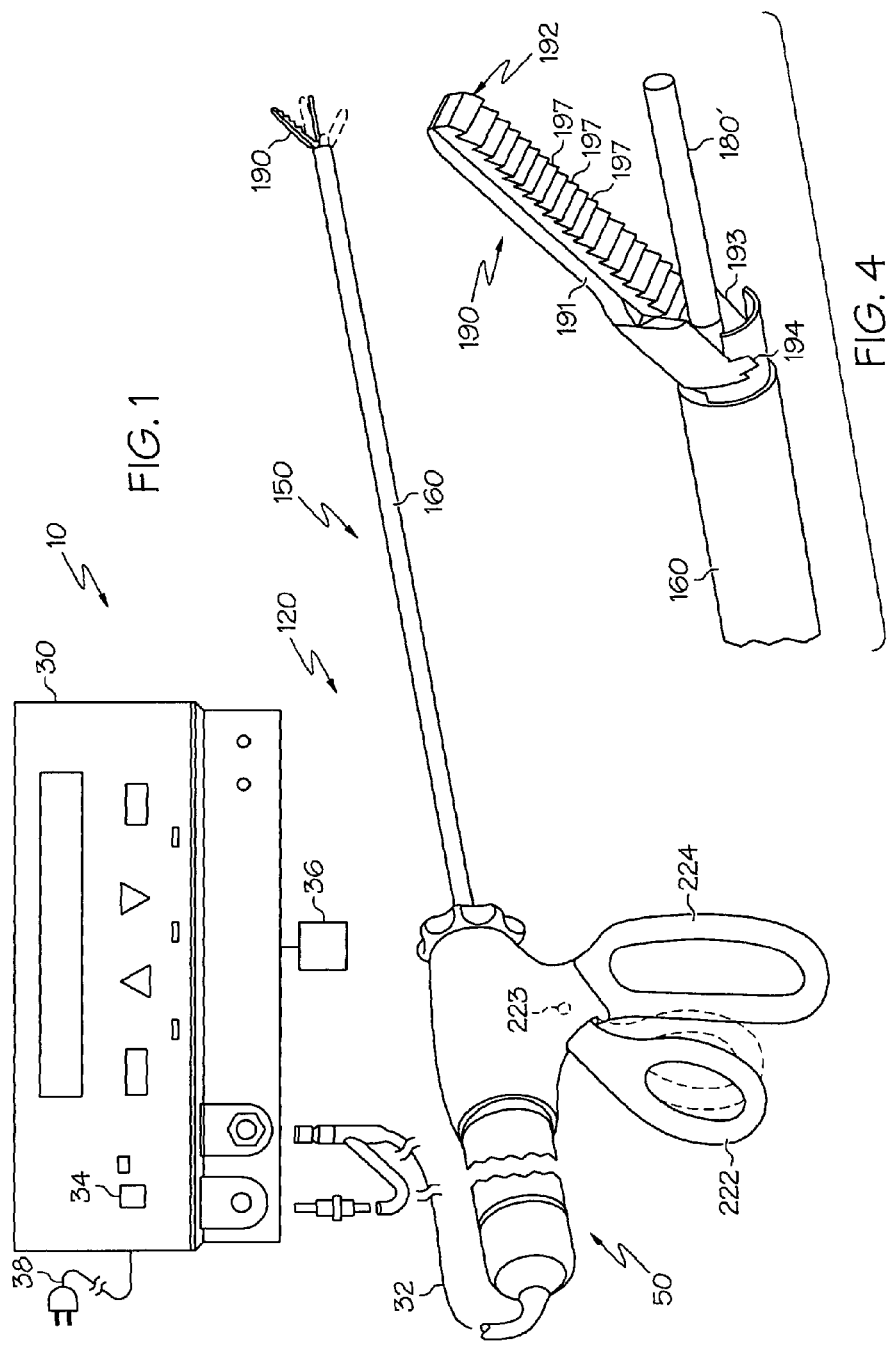
FIG. 1 illustrates one embodiment of a surgical system including a surgical instrument and an ultrasonic generator.

Before explaining the various embodiments in detail, it should be noted that the embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and blade configurations disclosed below are illustrative only and not meant to limit the scope or application thereof. Also, the blade and end effector designs described hereinbelow may be used in conjunction with any suitable device. Furthermore, unless otherwise indicated, the terms and expressions employed herein have been chosen for the purpose of describing the illustrative embodiments for the convenience of the reader and are not to limit the scope thereof.

Examples of ultrasonic surgical instruments and blades are disclosed in U.S. Pat. Nos. 5,322,055 and 5,954,736, 6,309,400 B2, 6,278,218B1, 6,283,981 B1, and 6,325,811 B1, which are incorporated herein by reference in their entirety. These references disclose ultrasonic surgical instrument designs and blade designs where a longitudinal mode of the blade is excited. The result is a longitudinal standing wave within the instrument. Accordingly, the instrument has nodes, where the transverse motion is equal to zero, and anti-nodes, where the transverse motion is at its maximum. The instrument's tissue end effector is often positioned at an anti-node to maximize its longitudinal motion.

Various embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

It will be appreciated that the terms "proximal" and "distal" are used herein with reference to a clinician gripping a surgical device at its hand piece assembly, or other comparable piece. Thus, the end effector is distal with respect to the more proximal hand piece assembly. It will be further appreciated that, for convenience and clarity, spatial terms such as "top" and "bottom" also are used herein with respect to the clinician gripping the hand piece assembly, or comparable piece. However, surgical instruments are used in many orientations and positions, and these terms are not intended to be limiting and absolute.

Figure 2:
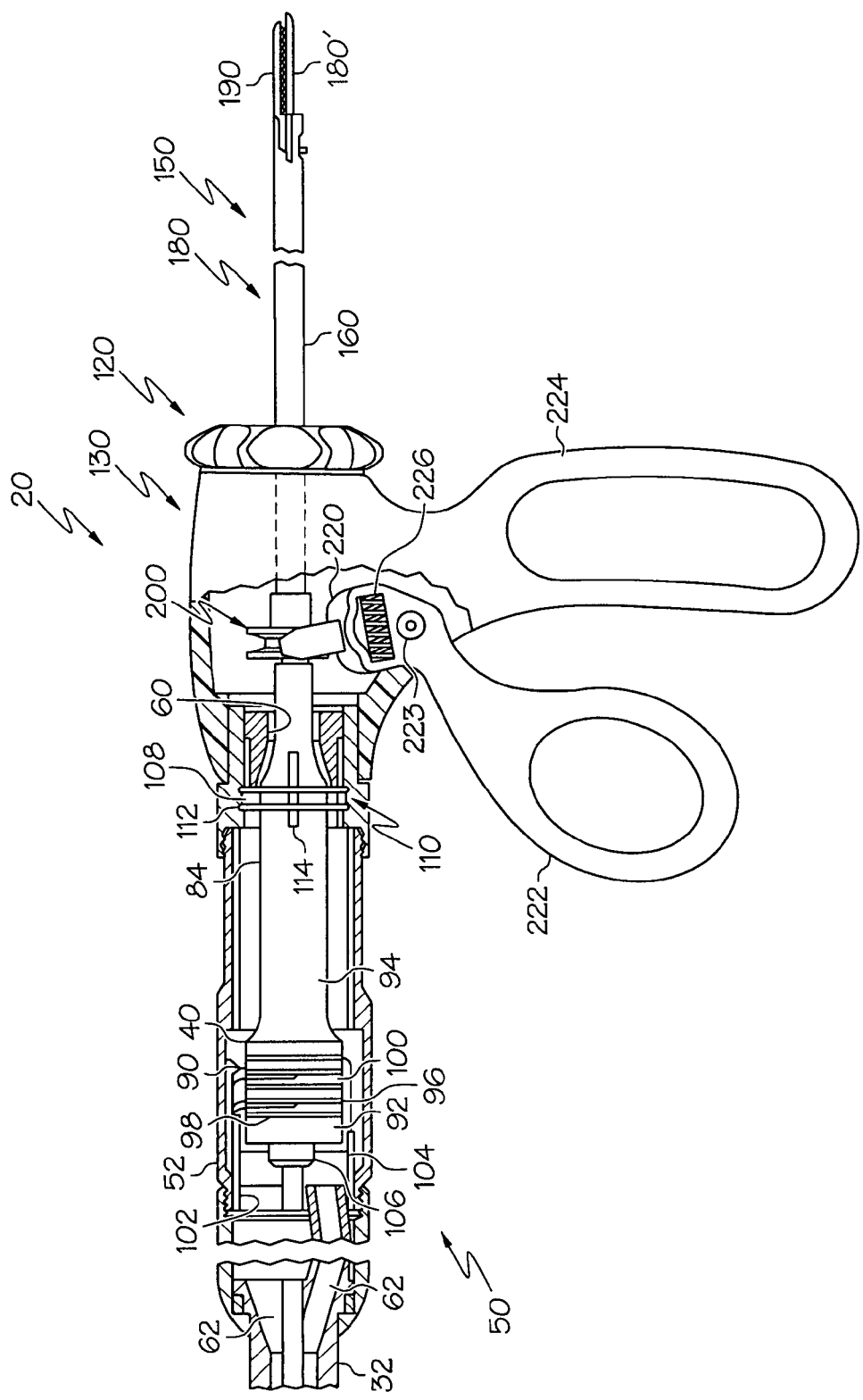
FIG. 2 illustrates one embodiment of the surgical instrument shown in FIG. 1.

FIG. 1 illustrates one embodiment of a surgical system including a surgical instrument and an ultrasonic generator. FIG. 2 illustrates one embodiment of the apparatus shown in FIG. 1. In the embodiment illustrated in FIGS. 1-2, the surgical system 10 includes an ultrasonic clamp coagulator instrument 120 and an ultrasonic generator 30. The surgical instrument 120 includes an ultrasonic drive unit 50. As will be further described, an ultrasonic transducer of the drive unit 50, and an ultrasonic end effector 180 of the clamp instrument 120, together provide an acoustic assembly of the surgical system 10, with the acoustic assembly providing ultrasonic energy for surgical procedures when powered by generator 30. It will be noted that, in some applications, the ultrasonic drive unit 50 is referred to as a "hand piece assembly" because the surgical instrument 120 of the surgical system 10 is configured such that a clinician grasps and manipulates the ultrasonic drive unit 50 during various procedures and operations. The instrument 120 may include a scissors-like grip arrangement which facilitates positioning and manipulation of the instrument 120 apart from manipulation of the ultrasonic drive unit 50.

The generator 30 of the surgical system 10 sends an electrical signal through a cable 32 at a selected excursion, frequency, and phase determined by a control system of the generator 30. As will be further described, the signal causes one or more piezoelectric elements of the acoustic assembly of the surgical instrument 120 to expand and contract along a longitudinal axis, thereby converting the electrical energy into mechanical motion. The mechanical motion results in longitudinal waves of ultrasonic energy that propagate through the acoustic assembly in an acoustic standing wave to vibrate the acoustic assembly at a selected frequency and excursion. The end effector 180 is placed in contact with tissue of the patient to transfer the ultrasonic energy to the tissue. For example, a distal portion of blade 180' of the end effector may be placed in contact with the tissue. As further described below, a surgical tool, such as, a jaw or clamping mechanism, may be utilized to press the tissue against the blade 180'.

As the end effector 180 couples with the tissue, thermal energy or heat is generated as a result of friction, acoustic absorption, and viscous losses within the tissue. The heat is sufficient to break protein hydrogen bonds, causing the highly structured protein (e.g., collagen and muscle protein) to denature (e.g., become less organized). As the proteins are denatured, a sticky coagulum forms to seal or coagulate small blood vessels. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the excursion of the end effector 180, the frequency of vibration, the amount of pressure applied by the user, the sharpness of the end effector 180, and the coupling between the end effector 180 and the tissue.

In the embodiment illustrated in FIG. 1, the generator 30 includes a control system integral with the generator 30, a power switch 34, and a triggering mechanism 36. The power switch 34 controls the electrical power to the generator 30, and when activated by the triggering mechanism 36, the generator 30 provides energy to drive the acoustic assembly of the surgical system 10 frequency and to drive the end effector 180 at a predetermined excursion level. The generator 30 drives or excites the acoustic assembly at any suitable resonant frequency of the acoustic assembly.

When the generator 30 is activated via the triggering mechanism 36, electrical energy is continuously applied by the generator 30 to a transducer stack or assembly 40 of the acoustic assembly. A phase-locked loop in the control system of the generator 30 monitors feedback from the acoustic assembly. The phase lock loop adjusts the frequency of the electrical energy sent by the generator 30 to match the resonant frequency of the selected longitudinal mode of vibration of the acoustic assembly. In addition, a second feedback loop in the control system maintains the electrical current supplied to the acoustic assembly at a pre-selected constant level in order to achieve substantially constant excursion at the end effector 180 of the acoustic assembly.

The electrical signal supplied to the acoustic assembly will cause the distal end of the end effector 180, e.g., the blade 180', to vibrate longitudinally in the range of, for example, approximately 20 kHz to 250 kHz. According to various embodiments, the blade 180' may vibrate in the range of about 54 kHz to 56 kHz, for example, at about 55.5 kHz. In other embodiments, the blade 180' may vibrate at other frequencies including, for example, about 31 kHz or about 80 kHz. The excursion of the vibrations at the blade can be controlled by, for example, controlling the amplitude of the electrical signal applied to the transducer assembly 40 of the acoustic assembly by the generator 30.

As noted above, the triggering mechanism 36 of the generator 30 allows a user to activate the generator 30 so that electrical energy may be continuously supplied to the acoustic assembly. The triggering mechanism 36 may comprise a foot activating switch that is detachably coupled or attached to the generator 30 by a cable or cord. Alternatively, the triggering mechanism can be configured as a hand switch incorporated in the ultrasonic drive unit 50 to allow the generator 30 to be activated by a user.

The generator 30 also has a power line 38 for insertion in an electro-surgical unit or conventional electrical outlet. It is contemplated that the generator 30 can also be powered by a direct current (DC) source, such as a battery. The generator 30 can comprise any suitable generator, such as Model No. GEN04, available from Ethicon Endo-Surgery, Inc.

Figure 3:
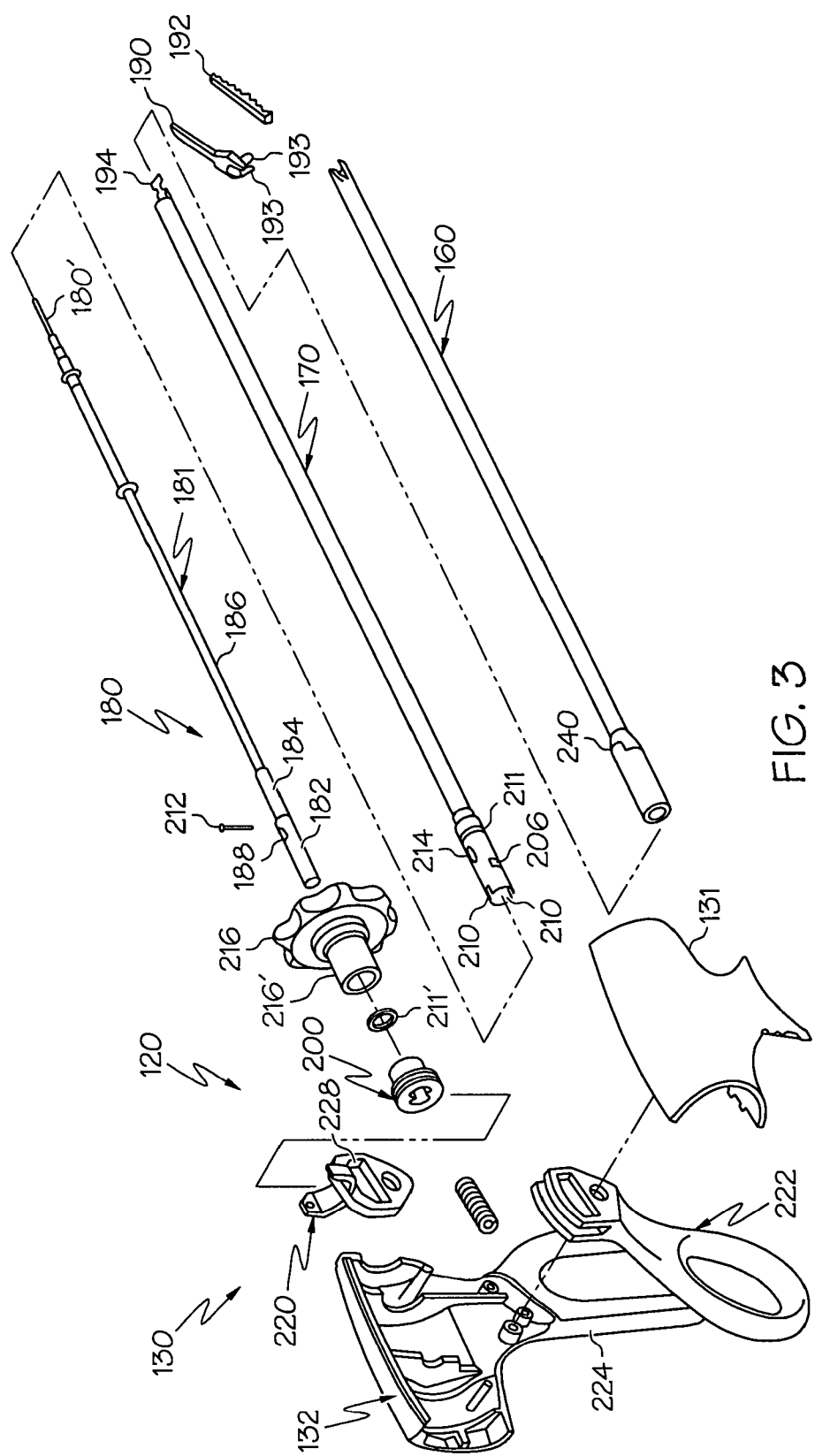
FIG. 3 illustrates an exploded view of one embodiment the surgical instrument shown in FIG. 1.

In the embodiment illustrated in FIGS. 1 and 3, the ultrasonic drive unit 50 of the surgical instrument includes a multi-piece housing 52 adapted to isolate the operator from the vibrations of the acoustic assembly. The drive unit housing 52 can be shaped to be held by a user in a conventional manner, but it is contemplated that the present clamp coagulator instrument 120 principally be grasped and manipulated by a scissors-like arrangement provided by a housing of the apparatus, as will be described. While the multi-piece housing 52 is illustrated, the housing 52 may comprise a single or unitary component.

The housing 52 of the ultrasonic drive unit 50 generally includes a proximal end, a distal end, and a cavity extending longitudinally therein. The distal end of the housing 52 includes an opening 60 configured to allow the acoustic assembly of the surgical system 10 to extend therethrough, and the proximal end of the housing 52 is coupled to the generator 30 by the cable 32. The cable 32 may include ducts or vents 62 to allow air or other fluids to be introduced into the housing 52 of the ultrasonic drive unit 50 to cool the transducer assembly 40 of the acoustic assembly.

The housing 52 of the ultrasonic drive unit 50 may be constructed from a durable plastic, such as ULTEM®. It is also contemplated that the housing 52 may alternatively be made from a variety of materials including other plastics (e.g. liquid crystal polymer (LCP), nylon, or polycarbonate) and/or metals (e.g., aluminum, steel, etc.). A suitable ultrasonic drive unit 50 is Model No. HP054, available from Ethicon Endo-Surgery, Inc.

The acoustic assembly of the surgical instrument generally includes a first acoustic portion and a second acoustic portion. The first acoustic portion may be carried by the ultrasonic drive unit 50, and the second acoustic portion (in the form of an end effector 180, as will be described) is carried by the ultrasonic clamp coagulator 120. The distal end of the first acoustic portion is operatively coupled to the proximal end of the second acoustic portion, preferably by a threaded connection.

In the embodiment illustrated in FIG. 2, the first acoustic portion includes the transducer stack or assembly 40 and a mounting device 84, and the second acoustic portion includes the end effector 180. The end effector 180 may in turn comprise a transmission component, or waveguide 181 (FIG. 3), as well as a distal portion, or blade 180', for interfacing with tissue.

The components of the acoustic assembly may be acoustically tuned such that the length of each component is an integral number of one-half wavelengths ($n\lambda/2$), where the wavelength $\lambda$ is the wavelength of a pre-selected or operating longitudinal vibration frequency $f_0$ of the acoustic assembly, and n is any non-negative integer. It is also contemplated that the acoustic assembly may incorporate any suitable arrangement of acoustic elements.

The transducer assembly 40 of the acoustic assembly converts the electrical signal from the generator 30 into mechanical energy that results in longitudinal vibratory motion of the end effector 180 at ultrasonic frequencies. When the acoustic assembly is energized, a vibratory motion standing wave is generated through the acoustic assembly. The excursion of the vibratory motion at any point along the acoustic assembly depends on the location along the acoustic assembly at which the vibratory motion is measured. A minimum or zero crossing in the vibratory motion standing wave is generally referred to as a node (e.g., where motion is usually minimal), and a local absolute value maximum or peak in the standing wave is generally referred to as an anti-node. The distance between an anti-node and its nearest node is one-quarter wavelength ($\lambda/4$).

In the embodiment illustrated in FIG. 2, the transducer assembly 40 of the acoustic assembly, which is also known as a "Langevin stack", generally includes a transduction portion 90, a first resonator 92, and a second resonator 94. The transducer assembly 40 may be an integral number of one-half system wavelengths ($n\lambda/2$) in length. It is to be understood that other embodiments of the transducer assembly 40 may comprise a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 may be fabricated from titanium, aluminum, steel, or any other suitable material, and most preferably, the first resonator 92 is fabricated from 303 stainless steel and the second resonator 94 is fabricated from 7075-T651 Aluminum. The first and second resonators 92 and 94 have a length determined by a number of variables, including the length of the transduction section 90, the speed of sound of material used in the resonators 92 and 94, and the desired fundamental frequency $f_o$ of the transducer assembly 40. The second resonator 94 can be tapered inwardly from its proximal end to its distal end to function as a velocity transformer and amplify the ultrasonic vibration excursion.

The transduction portion 90 of the transducer assembly 40 may comprise a piezoelectric section of alternating positive electrodes 96 and negative electrodes 98, with the piezoelectric elements 100 alternating between the electrodes 96 and 98. The piezoelectric elements 100 can be fabricated from any suitable material, such as, for example, lead zirconate-titanate, lead metaniobate, lead titanate, or other piezoelectric material. Each of the positive electrodes 96, negative electrodes 98, and piezoelectric elements 100 have a bore extending through the center. The positive and negative electrodes 96 and 98 are electrically coupled to wires 102 and 104, respectfully. The wires 102 and 104 transmit the electrical signal from the generator 30 to the electrodes 96 and 98.

The piezoelectric elements 100 may be held in compression between the first and second resonators 92 and 94 by a bolt 106. The bolt 106 may have a head, a shank, and a threaded distal end. The bolt 106 may be inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94. The bolt 106 may be fabricated from steel, titanium, aluminum, or other suitable material. For example, the bolt 106 may be fabricated from Ti-6Al-4V Titanium or from 4037 low alloy steel.

The piezoelectric elements 100 may be energized in response to the electrical signal supplied from the generator 30 to produce an acoustic standing wave in the acoustic assembly. The electrical signal causes an electromagnetic field across the piezoelectric elements 100, causing the piezoelectric elements 100 to expand and contract in a continuous manner along the longitudinal axis of the voltage gradient, producing high frequency longitudinal waves of ultrasonic energy. The ultrasonic energy is transmitted through the acoustic assembly to the end effector 180.

The mounting device 84 of the acoustic assembly has a proximal end, a distal end, and may have a length substantially equal to an integral number of one-half system wavelengths ($n\lambda/2$). The proximal end of the mounting device 84 may be axially aligned and coupled to the distal end of the second resonator 94 by an internal threaded connection near an anti-node. It is also contemplated that the mounting device 84 may be attached to the second resonator 94 by any suitable means, and the second resonator 94 and mounting device 84 may be formed as a single or unitary component.

The mounting device 84 is coupled to the housing 52 of the ultrasonic drive unit 50 near a node. The mounting device 84 may include an integral mounting flange 108 disposed around its periphery. The mounting flange 108 may be disposed in an annular groove 110 formed in the housing 52 of the ultrasonic drive unit 50 to couple the mounting device 84 to the housing 52. A compliant member or material 112, such as a pair of silicone rubber O-rings attached by stand-offs, may be placed between the annular groove 110 of the housing 52 and the integral flange 108 of the mounting device 86 to reduce or prevent ultrasonic vibration from being transmitted from the mounting device 84 to the housing 52.

The mounting device 84 may be secured in a predetermined axial position by a plurality of pins 114, for example, four. The pins 114 are disposed in a longitudinal direction ninety (90) degrees apart from each other around the outer periphery of the mounting device 84. The pins 114 are coupled to the housing 52 of the ultrasonic drive unit 50 and are disposed through notches in the acoustic mounting flange 108 of the mounting device 84. The pins 114 may be fabricated from stainless steel. According to various embodiments, the pins 114 may be formed as integral components of the housing 52.

The mounting device 84 may be configured to amplify the ultrasonic vibration excursion that is transmitted through the acoustic assembly to the distal end of the end effector 180. In one embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 be configured as any suitable shape, such as, for example, a stepped horn, a conical horn, an exponential horn, a unitary gain horn, or the like.

The mounting device 84 may be acoustically coupled to the second acoustic portion of the ultrasonic clamp coagulator instrument 120. The distal end of the mounting device 84 may be coupled to the proximal end of the second acoustic portion by an internal threaded connection near an anti-node, but alternative coupling arrangements can be employed.

FIG. 3 illustrates an exploded view of one embodiment the surgical instrument shown in FIG. 1. The proximal end of the ultrasonic clamp coagulator instrument 120 preferably receives and is fitted to the distal end of the ultrasonic drive unit 50 by insertion of the drive unit 50 into the housing 52, as shown in FIG. 2. The ultrasonic clamp coagulator instrument 120 may be attached to and removed from the ultrasonic drive unit 50 as a unit. The ultrasonic clamp coagulator 120 may be disposed of after a single use.

The ultrasonic clamp coagulator instrument 120 may include a handle assembly or a housing 130, which may comprise mating housing portions 131, 132, and an elongated or endoscopic portion 150. When the present apparatus is configured for endoscopic use, the construction can be dimensioned such that portion 150 has an outside diameter of about 5.5 mm. The elongated portion 150 of the ultrasonic clamp coagulator instrument 120 may extend substantially orthogonally from the apparatus housing 130. The elongated portion 150 can be selectively rotated with respect to the housing 130 as described below. The elongated portion 150 may include an outer tubular member or sheath 160, an inner tubular actuating member 170, and the second acoustic portion of the acoustic system in the form of an end effector 180 including a blade 180'. As will be described, the outer sheath 160, the actuating member 170, and the end effector 180 may be joined together for indexed rotation as a unit (together with ultrasonic drive unit 50) relative to housing 130.

The proximal end of the end effector 180 of the second acoustic portion may be detachably coupled to the mounting device 84 of the ultrasonic drive unit 50 near an anti-node as described above. The end effector 180 may have a length substantially equal to an integer number of one-half system wavelengths ($n\lambda/2$). The end effector 180 may be fabricated from a solid core shaft constructed out of material which propagates ultrasonic energy efficiently, such as a titanium alloy (e.g., Ti-6Al-4V) or an aluminum alloy. It is contemplated that the end effector 180 can alternatively be fabricated from any other suitable material.

As described, the end effector 180 may include a waveguide 181. The waveguide 181 may be substantially semi-flexible. It will be recognized that the waveguide 181 can alternatively be substantially rigid or may comprise a flexible wire. The waveguide 181 may be configured to amplify the mechanical vibrations transmitted through the waveguide to the blade as is well known in the art. The waveguide 181 may further have features to control the gain of the longitudinal vibration along the waveguide 181 and features to tune the waveguide to the resonant frequency of the system.

It will be recognized that the end effector 180 may have any suitable cross-sectional dimension. For example, the end effector 180 may have a substantially uniform cross-section or the end effector 180 may be tapered at various sections or may be tapered along its entire length.

Referring now to FIG. 3, the waveguide 181 portion of the end effector 180 is shown to comprise a first section 182, a second section 184, and a third section 186. The first section 182 of may extend distally from the proximal end of the end effector 180, and has a substantially continuous cross-section dimension. The first section 182 may include at least one radial hole or aperture 188 extending diametrically therethrough, substantially perpendicular to the axis of the end effector 180. The aperture 188 may be positioned at a node, but may be otherwise positioned. It will be recognized that the aperture 188 may have any suitable depth and may be any suitable shape. The aperture 188 is configured to receive a connector pin member which connects the wave guide 181, the tubular actuating member 170, and the tubular outer sheath 160 together for conjoint, indexed rotation relative to apparatus housing 130.

The second section 184 of the wave guide 181 extends distally from the first section 182. The second section 184 preferably also has a substantially continuous cross-section. The diameter of the second section 184 may be smaller than the diameter of the first section 182 and larger than the diameter of the third section 186. As ultrasonic energy passes from the first section 182 of the end effector 180 into the second section 184, narrowing of the second section 184 will result in an increased amplitude of the ultrasonic energy passing therethrough.

The third section 186 extends distally from the distal end of the second section 184. The third section 186 also has a substantially continuous cross-section. The third section 186 also may include small diameter changes along its length. According to various embodiments, the transition from the second section 184 to the third section 186 may be positioned at an anti-node so that the diameter change in the third section does not bring about an increase in the amplitude of vibration.

The third section 186 may have a plurality of grooves or notches (not shown) formed in its outer circumference. The grooves may be located at nodes of the end effector 180 to act as alignment indicators for the installation of a damping sheath (not shown) and stabilizing silicone rings or compliant supports during manufacturing. A seal may be provided at the distal-most node, nearest the blade 180', to abate passage of tissue, blood, and other material in the region between the waveguide and actuating member 170.

The blade 180' of the end effector 180 may be integral therewith and formed as a single unit. The blade 180' may alternately be connected by a threaded connection, or by a welded joint. According to various embodiments, the blade 180' may be mechanically sharp or mechanically blunt. The distal end of the blade 180' is disposed near an anti-node in order to tune the acoustic assembly to a preferred resonant frequency $f_0$ when the acoustic assembly is not loaded by tissue. When the transducer assembly is energized, the distal end of the blade 180' is configured to move longitudinally in the range of, for example, approximately 10-500 microns peak-to-peak, and preferably in the range of about 10 to about 100 microns at a predetermined vibrational frequency $f_0$.

In accordance with the illustrated embodiment, the blade 180' may be cylindrical for cooperation with the associated clamping mechanism of the clamp coagulator 120. The end effector 180 may receive suitable surface treatment, as is known in the art.

FIG. 4 illustrates one embodiment of a clamping mechanism that may be used with the surgical instrument shown in FIG. 1. The clamping mechanism may be configured for cooperative action with the blade 180' of the end effector 180. The clamping mechanism includes a pivotally movable clamp arm 190, which is pivotally connected at the distal end thereof to the distal end of outer tubular sheath 160. The clamp arm 190 includes a clamp arm tissue pad 192, preferably formed from TEFLON® or other suitable low-friction material, which is mounted for cooperation with the blade 180', with pivotal movement of the clamp arm 190 positioning the clamp pad 192 in substantially parallel relationship to, and in contact with, the blade 180'. By this construction, tissue to be clamped is grasped between the tissue pad 192 and the blade 180'. The tissue pad 192 may be provided with a sawtooth-like configuration including a plurality of axially spaced, proximally extending gripping teeth 197 to enhance the gripping of tissue in cooperation with the blade 180'.

Pivotal movement of the clamp arm 190 with respect to the blade 180' is effected by the provision of at least one, and preferably a pair of lever portions 193 of the clamp arm 190 at the proximal end thereof. The lever portions 193 are positioned on respective opposite sides of the end effector 180 and blade 180', and are in operative engagement with a drive portion 194 of the reciprocal actuating member 170. Reciprocal movement of the actuating member 170, relative to the outer tubular sheath 160 and the end effector 180, thereby effects pivotal movement of the clamp arm 190 relative to the blade 180'. The lever portions 193 can be respectively positioned in a pair of openings defined by the drive portion 194, or otherwise suitably mechanically coupled therewith, whereby reciprocal movement of the actuating member 170 acts through the drive portion 194 and lever portions 193 to pivot the clamp arm 190.

Figure 5:
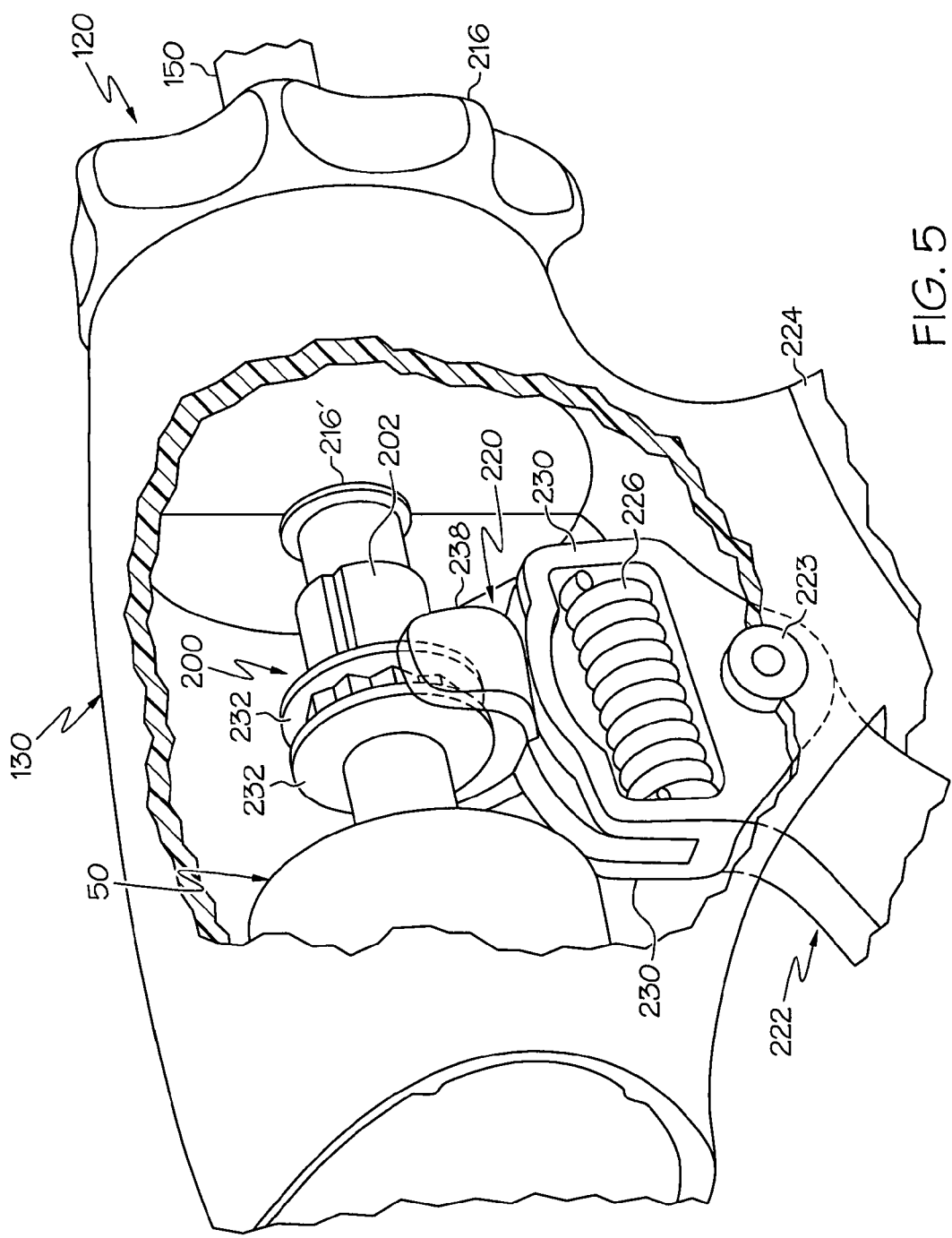
FIG. 5 illustrates a cut-away view of one embodiment of the surgical instrument shown in FIG. 1.
Figure 6:
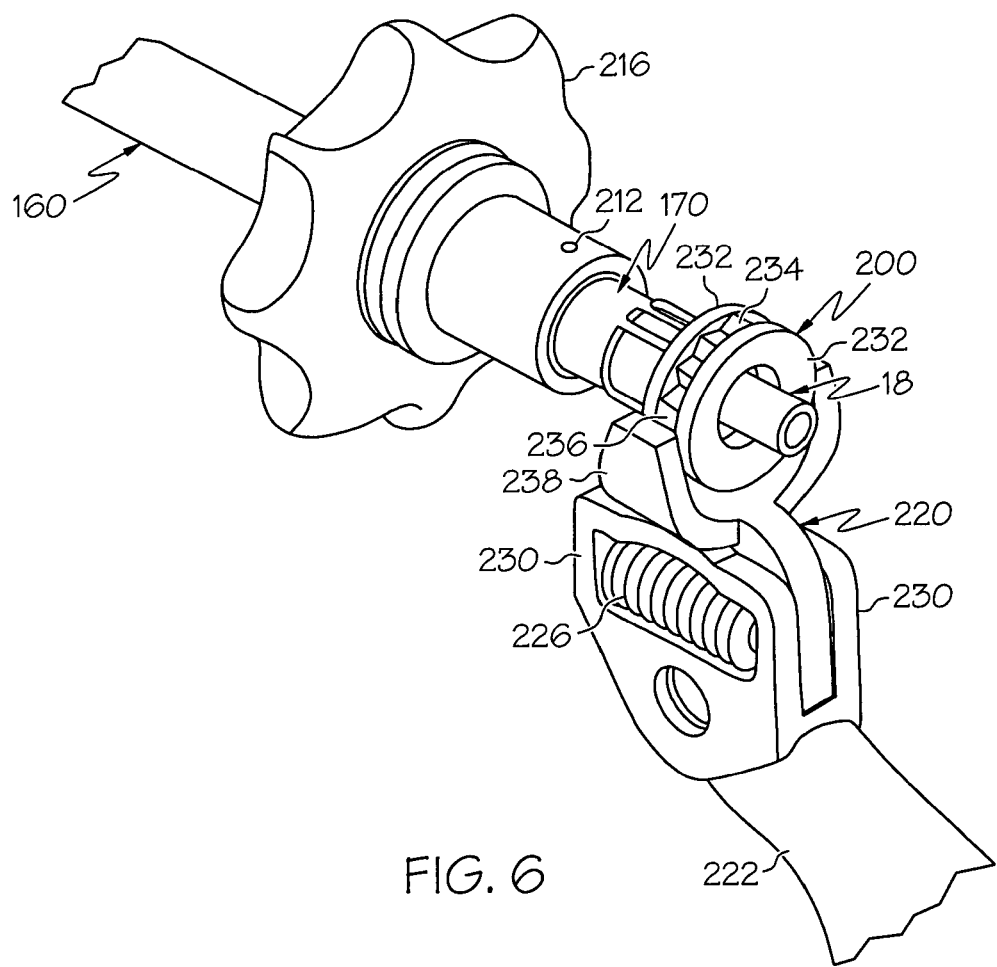
FIG. 6 illustrates various internal components of one embodiment of the surgical instrument shown in FIG. 1.
Figure 7:
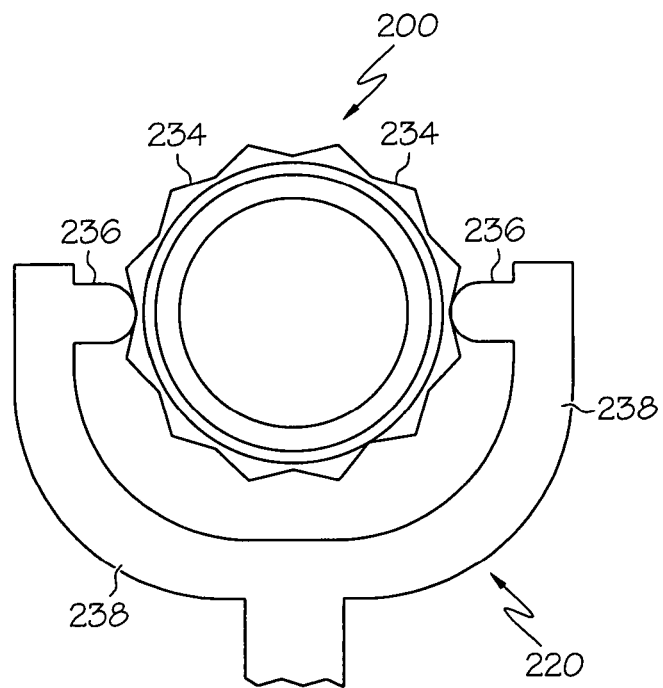
FIG. 7 illustrates one embodiment of a drive yoke of the surgical instrument shown in FIG. 1.
Figure 8:
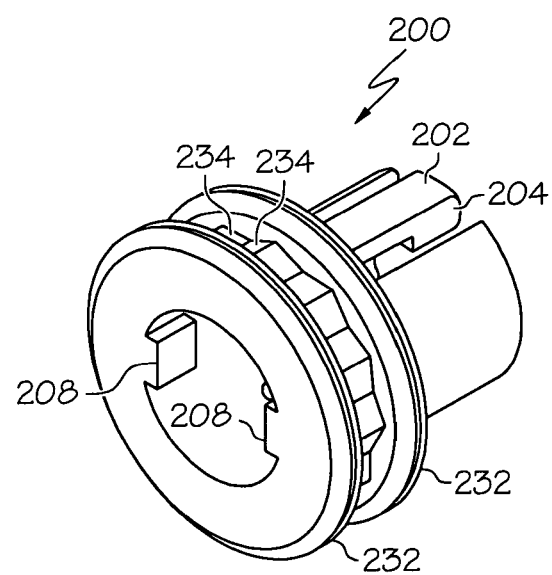
FIG. 8 illustrates one embodiment of a drive collar of the surgical instrument shown in FIG. 1.

FIG. 5 illustrates a cut-away view of one embodiment of the surgical instrument shown in FIG. 1, while FIG. 6 illustrates various internal components of one embodiment of the surgical instrument shown in FIG. 1. FIG. 7 illustrates one embodiment of a drive yoke, and FIG. 8 illustrates one embodiment of a drive collar of the surgical instrument shown in FIG. 1. In the embodiment illustrated in FIGS. 3 and 5-8, reciprocal movement of the actuating member 170 is effected by the provision of a drive collar 200 mounted on the proximal end of the actuating member 170 for conjoint rotation. The drive collar 200 may include a pair of diametrically opposed axially extending arms 202 each having a drive lug 204, with the drive lugs 204 being biased by the arms 202 into engagement with suitable openings 206 defined by the proximal portion of tubular actuating member 170. Rotation of the drive collar 200 together with the actuating member 170 is further effected by the provision of a pair of keys 208 diametrically engageable with suitable openings 210 defined by the proximal end of the actuating member 170. A circumferential groove 211 on the actuating member 170 receives an O-ring 211' (FIG. 3) for engagement with the inside surface of outer sheath 160.

Rotation of the actuating member 170 together with the tubular outer sheath 160 and inner end effector 180 is provided by a connector pin 212 extending through these components of the instrument 120. The tubular actuating member 170 defines an elongated slot 214 through which the connector pin 212 extends to accommodate reciprocal movement of the actuating member relative to the outer tubular sheath and inner waveguide.

A rotation knob 216 mounted on the outer tubular sheath facilitates rotational positioning of the elongated portion 150 with respect to the housing 130 of the clamp coagulator instrument 120. Connector pin 212 preferably joins the knob 216 together with the sheath 160, member 170, and the end effector 180 for rotation as a unit relative to the housing 130. In the embodiment, hub portion 216' of the rotation knob 216 acts to rotatably mount the outer sheath 160, the actuating member 170, and the end effector 180 (as a unit with the knob 216), on the housing 130.

The drive collar 200 provides a portion of the clamp drive mechanism of the instrument 120, which effects pivotal movement of the clamp arm 190 by reciprocation of the actuating member 170. The clamp drive mechanism further includes a drive yoke 220 which is operatively connected with an operating lever 222, with the operating lever thus interconnected with the reciprocal actuating member 170 via drive yoke 220 and drive collar 200. The operating lever 222 is pivotally connected to the housing 130 of the apparatus (by a pivot mount 223) for cooperation in a scissors-like fashion with a handgrip portion 224 of the housing. Movement of the lever 222 toward the handgrip portion 224 translates the actuating member 170 proximally, thereby pivoting the clamp arm 190 toward the blade 180'.

Operative connection of the drive yoke 220 with the operating lever 222 is provided by a spring 226, preferably comprising a compression coil spring 226. The spring 226 fits within a spring slot 228 defined by the drive yoke 220, which in turn is positioned between a pair of spring retainer flanges 230 of the operating lever 222. The drive yoke 220 is pivotally movable with respect to the spring flanges 230 (about pivot mount 223 of housing 130) in opposition to the compression coil spring, which bears against the surfaces of the spring slots defined by each of the spring flanges 230. In this manner, the force which can be applied to the actuating member 170, by pivotal movement of the operating lever 222 acting through the drive yoke 220 and the drive collar 200, is limited by the force with which the spring 226 bears against the spring flanges 230. Application of excessive force results in pivotal displacement of the drive yoke 220 relative to the spring flanges 230 of the operating lever 222 in opposition to spring 226. Stop portions of the housing 130 limit the travel of the operating lever 222 to prevent excessive compression of spring 226. In various embodiments, the force applied to the actuating member 170 may be limited by one or more springs (not shown) operatively positioned between the drive collar 200 and the member 170. For example, one or more cylindrical springs, such as a wave springs, may be used. An example embodiment utilizing a wave spring in this manner is described in U.S. Pat. No. 6,458,142, which is incorporated herein by reference.

Indexed rotational positioning of the elongated portion 150 of the present clamp coagulator instrument 120 may be provided by the provision of a detent mechanism incorporated into the clamp drive mechanism of the instrument 120. Specifically, the drive collar 200 may include a pair of axially spaced apart drive flanges 232. A detent-receiving surface may be provided between the drive flanges 232, and may define a plurality of circumferentially spaced teeth 234. The teeth 234 may define detent-receiving depressions generally about the periphery of the drive collar 200. In the embodiment illustrated in FIG. 7, twelve (12) of the teeth 234 are provided, thereby providing indexed positioning of the elongated portion 150 of the apparatus at 30° intervals relative to the housing 130 of the apparatus.

Indexed rotational movement may be further achieved by the provision of at least one, and preferably a pair, of diametrically opposed detents 236 respectively provided on cantilevered yoke arms 238 of the drive yoke 220. By this arrangement, the yoke arms 238 are positioned between the drive flanges 232 for engagement with the confronting surfaces thereof, and bias the detents 236 into engagement with the drive collar 200. Indexed relative rotation is thus achieved, with the detents 236 of the yoke arms 238 cooperating with the drive flanges 238 for effecting reciprocation of the actuating member 170. According to various embodiments, the drive yoke 220 may be formed from suitable polymeric material, with the biasing force created by the yoke arms 238 acting on the detents 236 thereof cooperating with the radial depressions defined by the drive collar to resist relative rotational torque less than about 5 to 20 inch-ounces. Accordingly, the elongated portion 150 of the clamp coagulator instrument 120 is maintained in any of its selected indexed rotational positions, relative to the housing 130, unless a torque is applied (such as by the rotation knob 216) exceeding this predetermined torque level. A snap-like indexing action is thus provided.

Rotation of the elongated proportion 150 of the present clamp coagulator instrument 120 may be effected together with relative rotational movement of ultrasonic drive unit 50 with respect to housing 130. In order to join the elongated portion 150 to the ultrasonic drive unit 50 in ultrasonic-transmitting relationship, the proximal portion of the outer tubular sheath 160 may be provided with a pair of wrench flats 240 (FIG. 3). The wrench flats allow torque to be applied by a suitable torque wrench or the like to thereby permit the end effector 180 to be joined to the ultrasonic drive unit 50. The ultrasonic drive unit 50, as well as the elongated portion 150, are thus rotatable, as a unit, by suitable manipulation of the rotation knob 216, relative to the housing 130 of the apparatus. The interior of housing 130 is dimensioned to accommodate such relative rotation of the drive unit 50.

Figure 9:
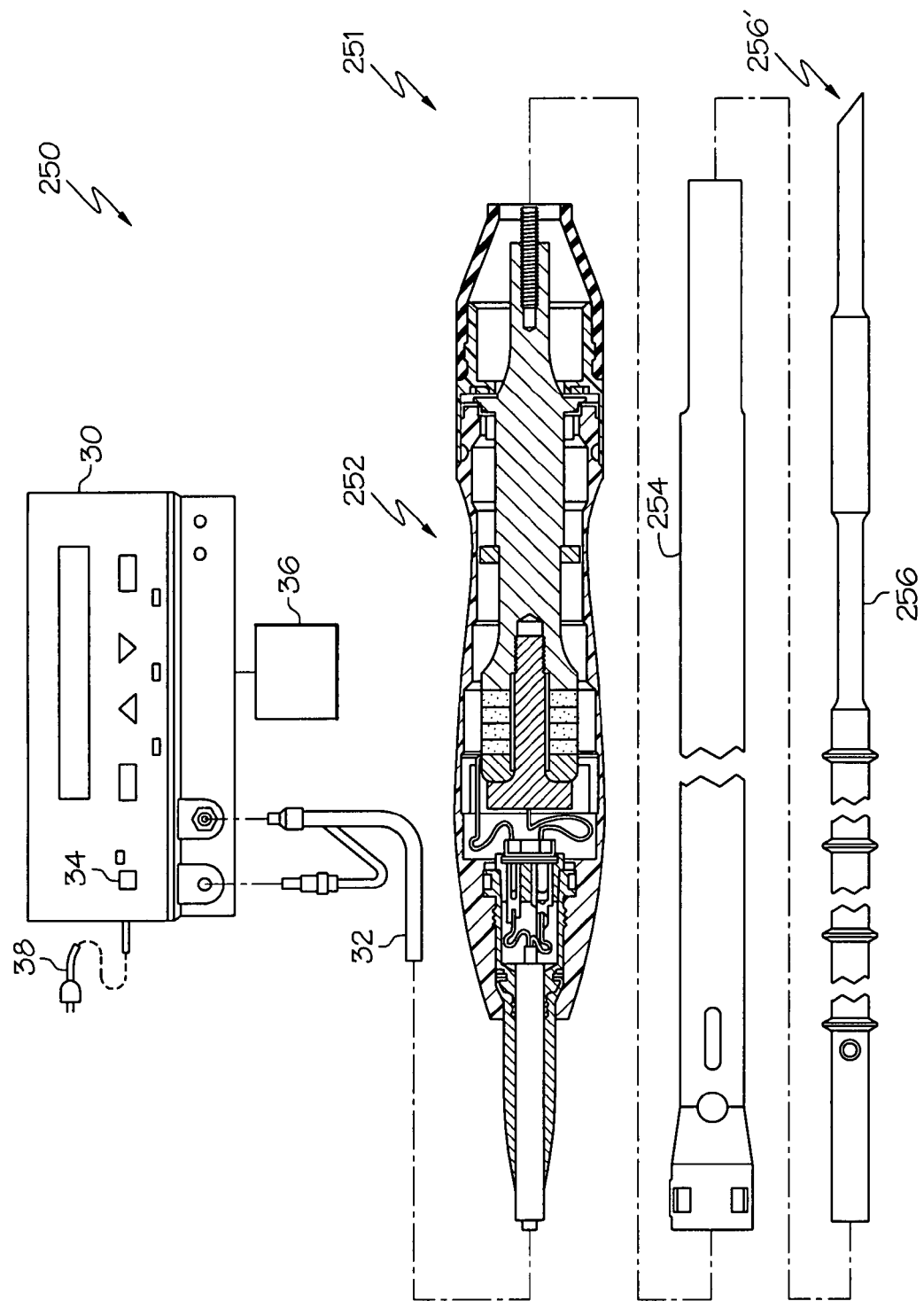
FIG. 9 illustrates one embodiment of a surgical system including a surgical instrument having single element end effector.

FIG. 9 illustrates one embodiment of a surgical system 250 including a surgical instrument 251 having single element end effector 256. The system 250 may include a transducer assembly 252 coupled to the end effector 256 and a sheath 254 positioned around the proximal portions of the end effector 256 as shown. The transducer assembly 252 and end effector 256 may operate in a manner similar to that of the transducer assembly 50 and end effector 180 described above to produce ultrasonic energy that may be transmitted to tissue via blade 256'

Figure 10:
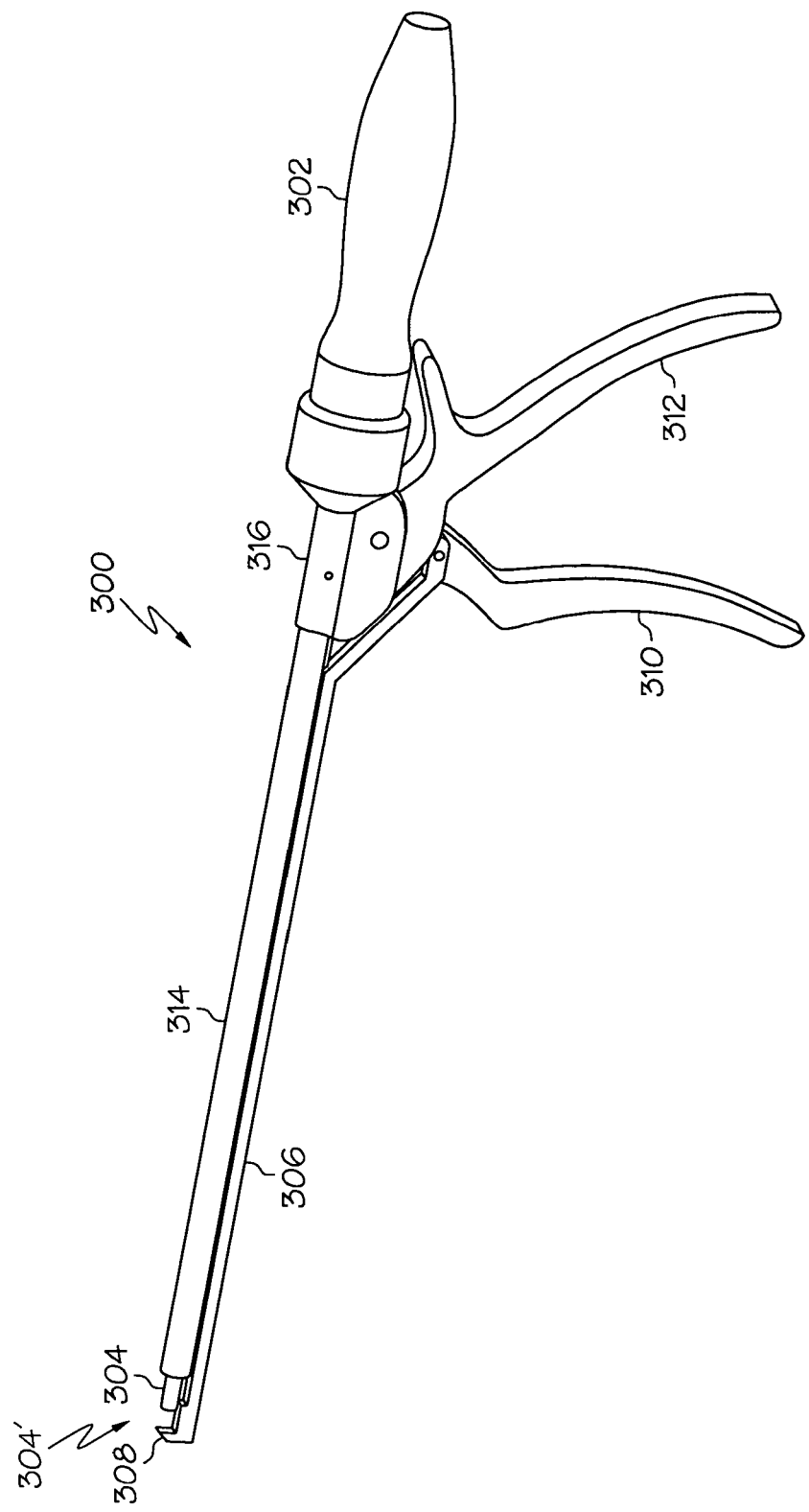
FIG. 10 illustrates one embodiment of a surgical device.
Figure 11:
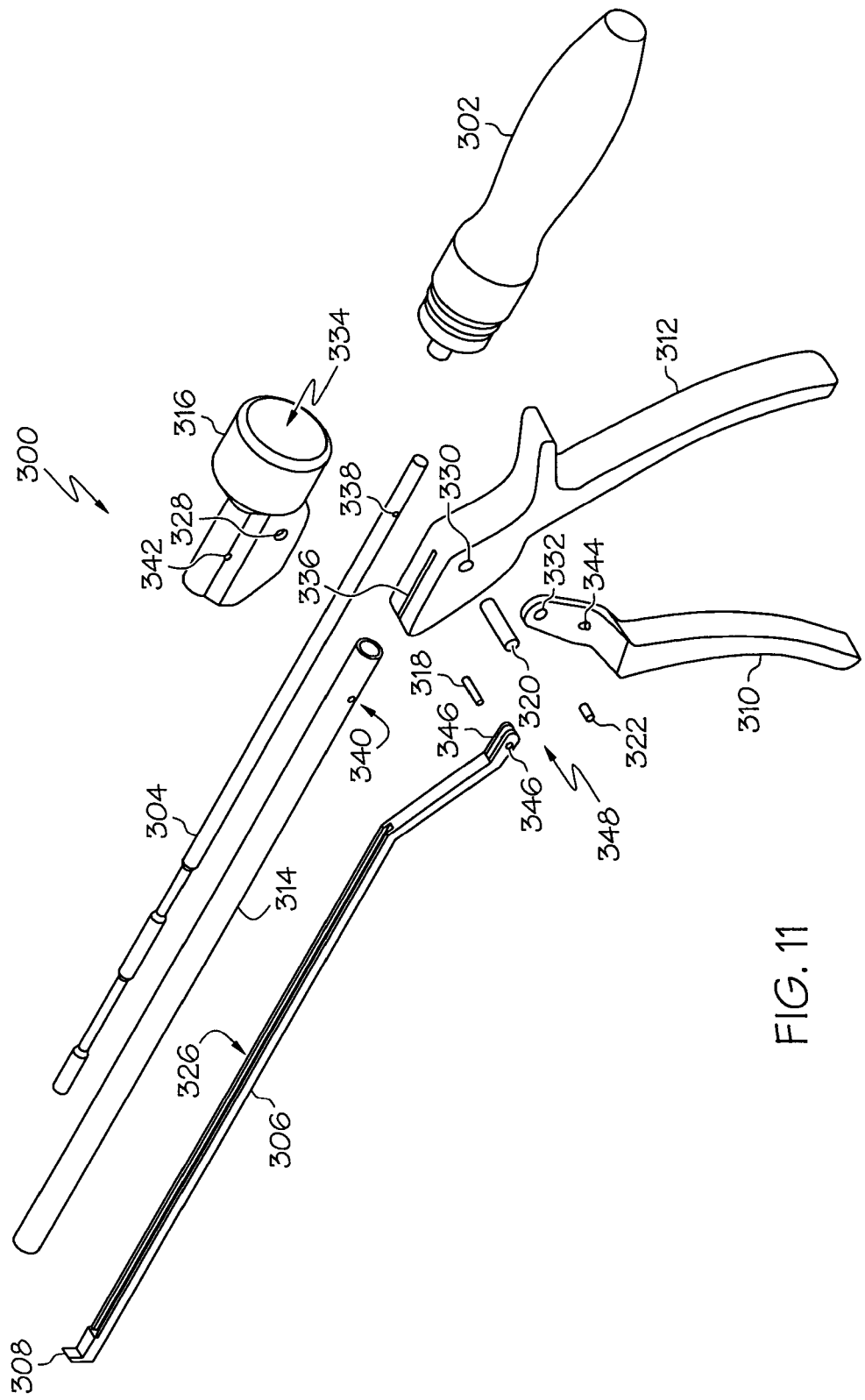
FIGS. 11-12 illustrate exploded views of one embodiment of the surgical device shown in FIG. 10.
Figure 12:
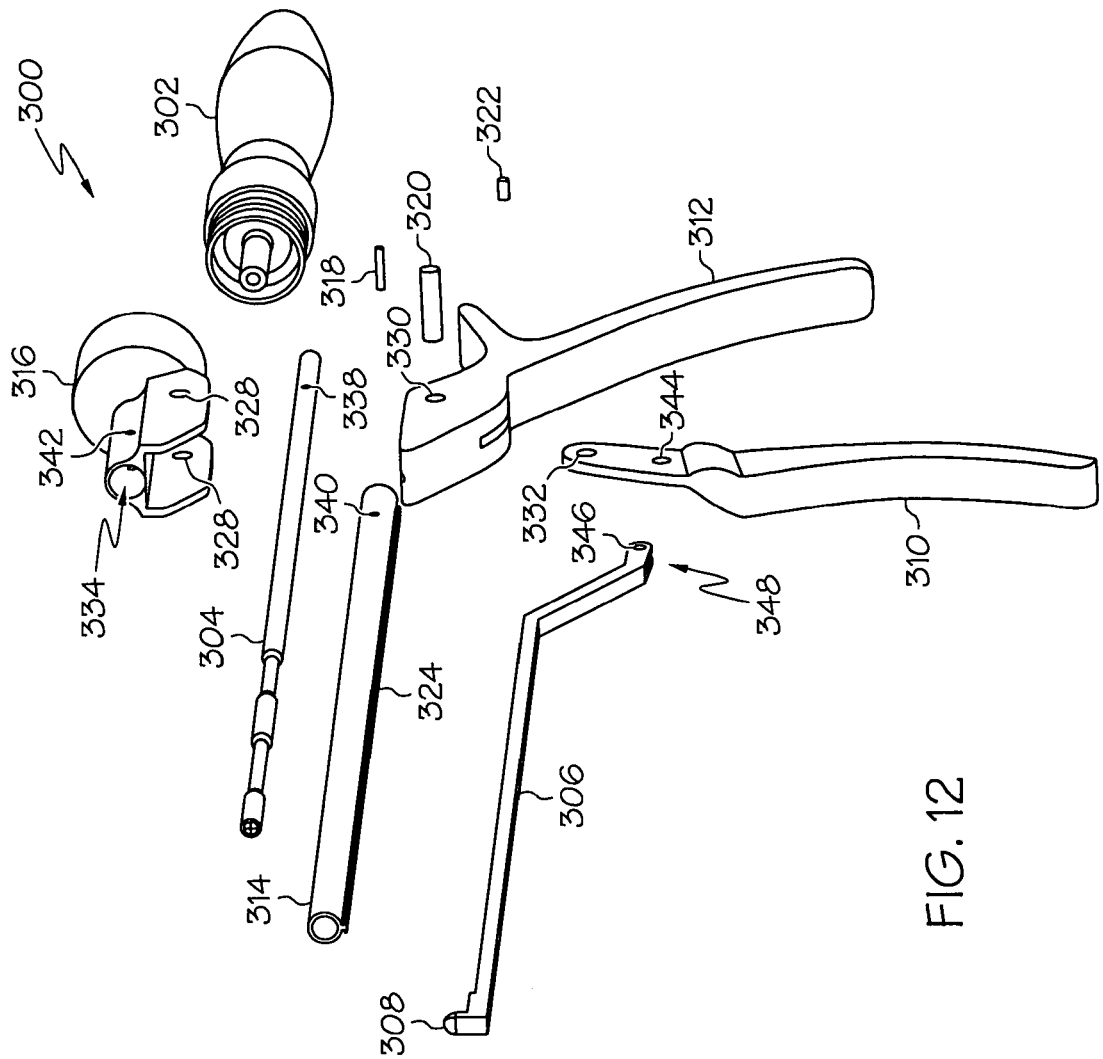

FIG. 10 illustrates one embodiment of a surgical device 300. FIGS. 11-12 illustrate exploded views of one embodiment of the surgical device 300 shown in FIG. 10. Generally, the surgical instrument 300 may comprise a transducer assembly 302, an end effector 304 and a lower jaw 306. The end effector 304 may be at least partially enclosed by a sheath 314. The lower jaw 306 may include a clamp face 308, and may be slidable relative to the end effector to bring the clamp face 308 toward a distal end of the end effector 304. According to various embodiments, the end effector 304 and/or the lower jaw 306 may define a lumen for aspirating a surgical site. Also, various blades 304' may be included with the end effector 304, for example, to bring about different surgical results.

Figure 13:
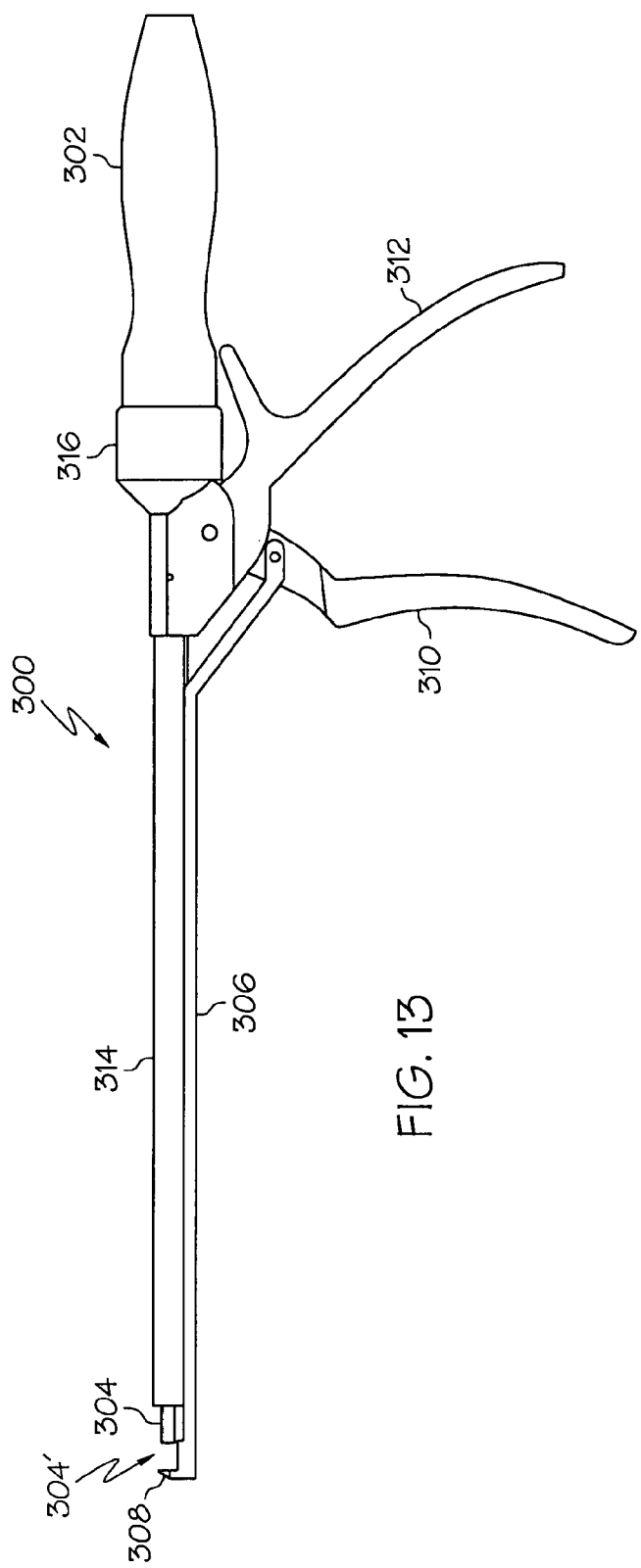
FIG. 13 illustrates a side view of one embodiment of the surgical device shown in FIG. 10 with the blade and clamp face separated from one another.
Figure 14:
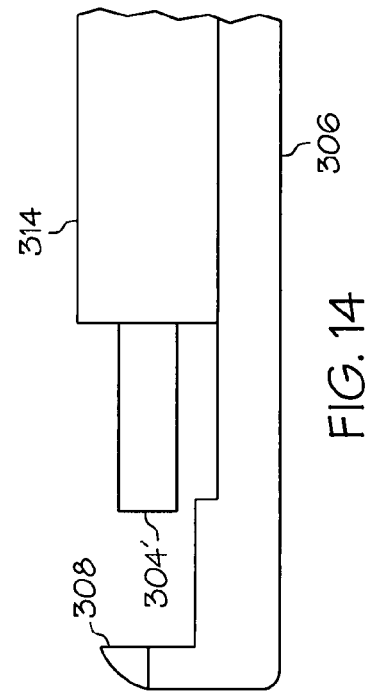
FIG. 14 illustrates a distal portion of one embodiment of the surgical device shown in FIG. 10 with the blade and clamp face separated from one another.
Figure 15:
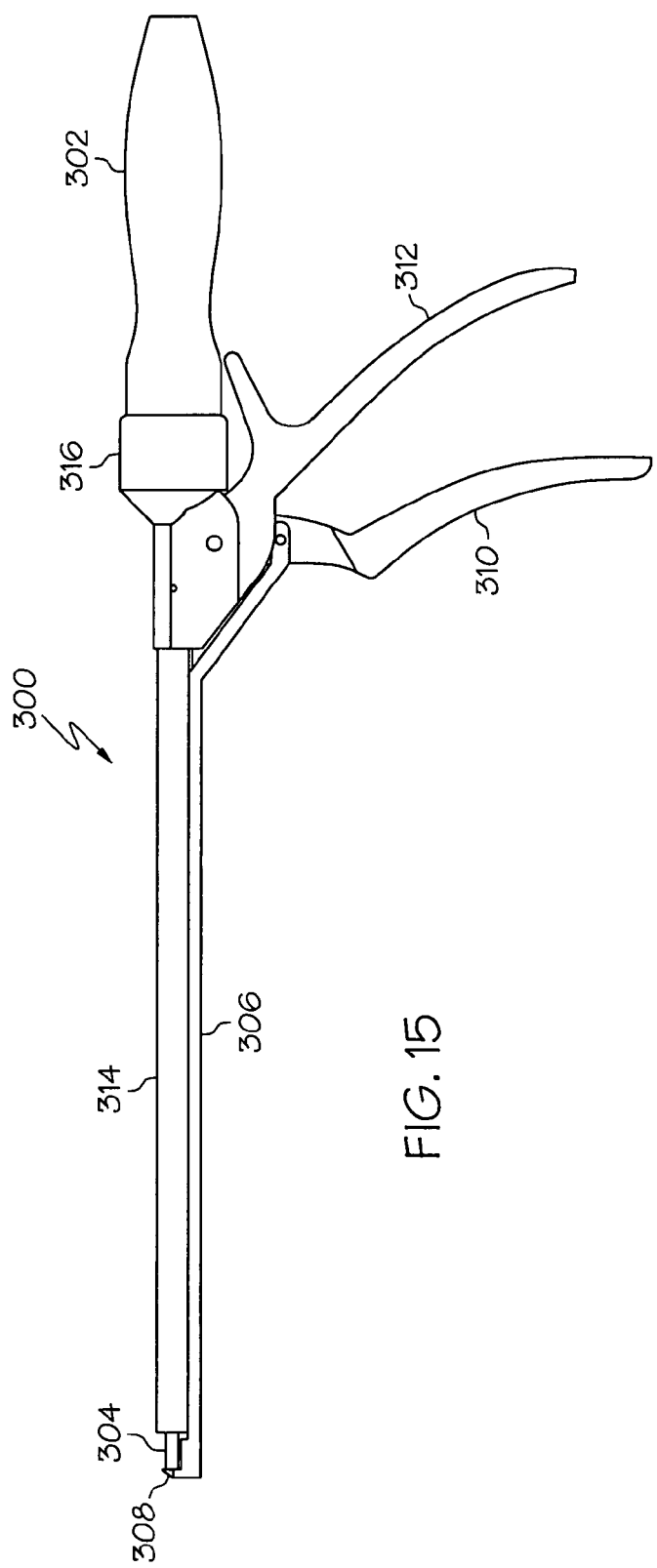
FIG. 15 illustrates a side view of one embodiment of the surgical device shown in FIG. 10 with the blade and clamp face translated toward one another.
Figure 16:
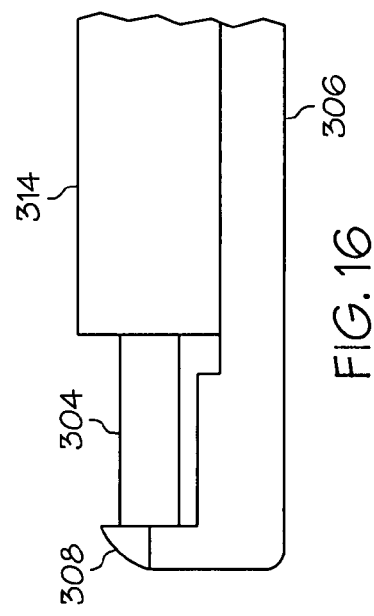
FIG. 16 illustrates a distal portion of one embodiment of the surgical device shown in FIG. 10 with the blade and clamp face translated toward one another.

FIGS. 13-14 illustrate one embodiment of the surgical device 300 shown in FIG. 10 configured in an open position with the blade 304' and clamp 308 separated from one another. In use, a clinician may introduce the device 300 to a surgical site the open position illustrated in FIGS. 13-14. When the device 300 is properly positioned, the clinician may transition the device 300 to a closed position, for example, by actuating a trigger 310. FIGS. 15-16 illustrate one embodiment of the surgical device 300 shown in FIG. 10 configured in a closed position with the blade 304' and clamp 308 translated towards one another. In the embodiment shown in FIGS. 15-16, the trigger has been rotated towards a handle 312, causing the lower jaw 306 to translate relative to the end effector 304, and bringing the clamp face 308 towards the blade 304'. In this way tissue may be clamped between the blade 304' and the clamp face 308. Energizing the end effector 304 may cause coagulation and/or cutting of the clamped tissue.

Figure 17:
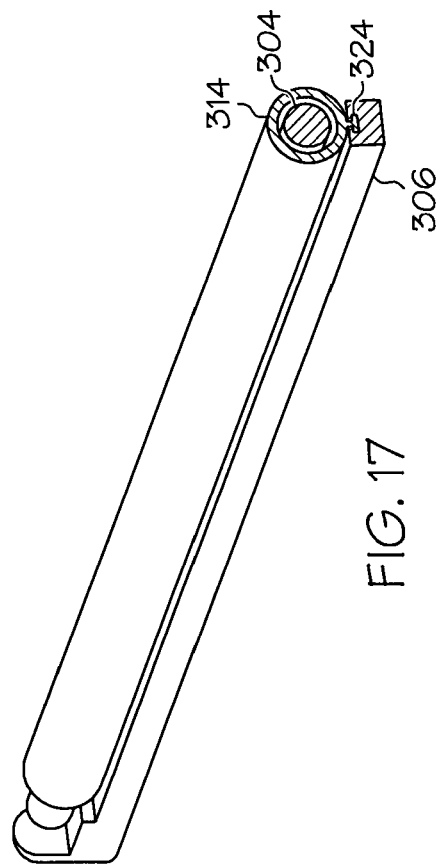
FIGS. 17-18 illustrate one embodiment of a lower jaw and outer sheath of the surgical device shown in FIG. 10.
Figure 18:
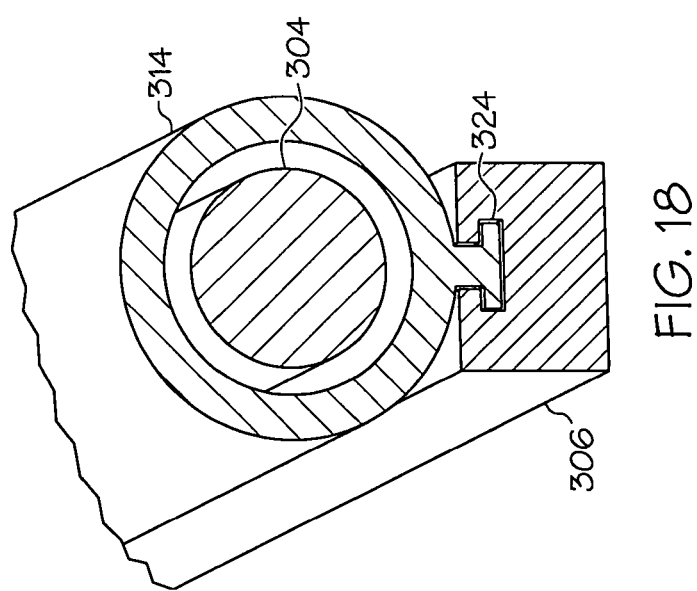
Figure 19:
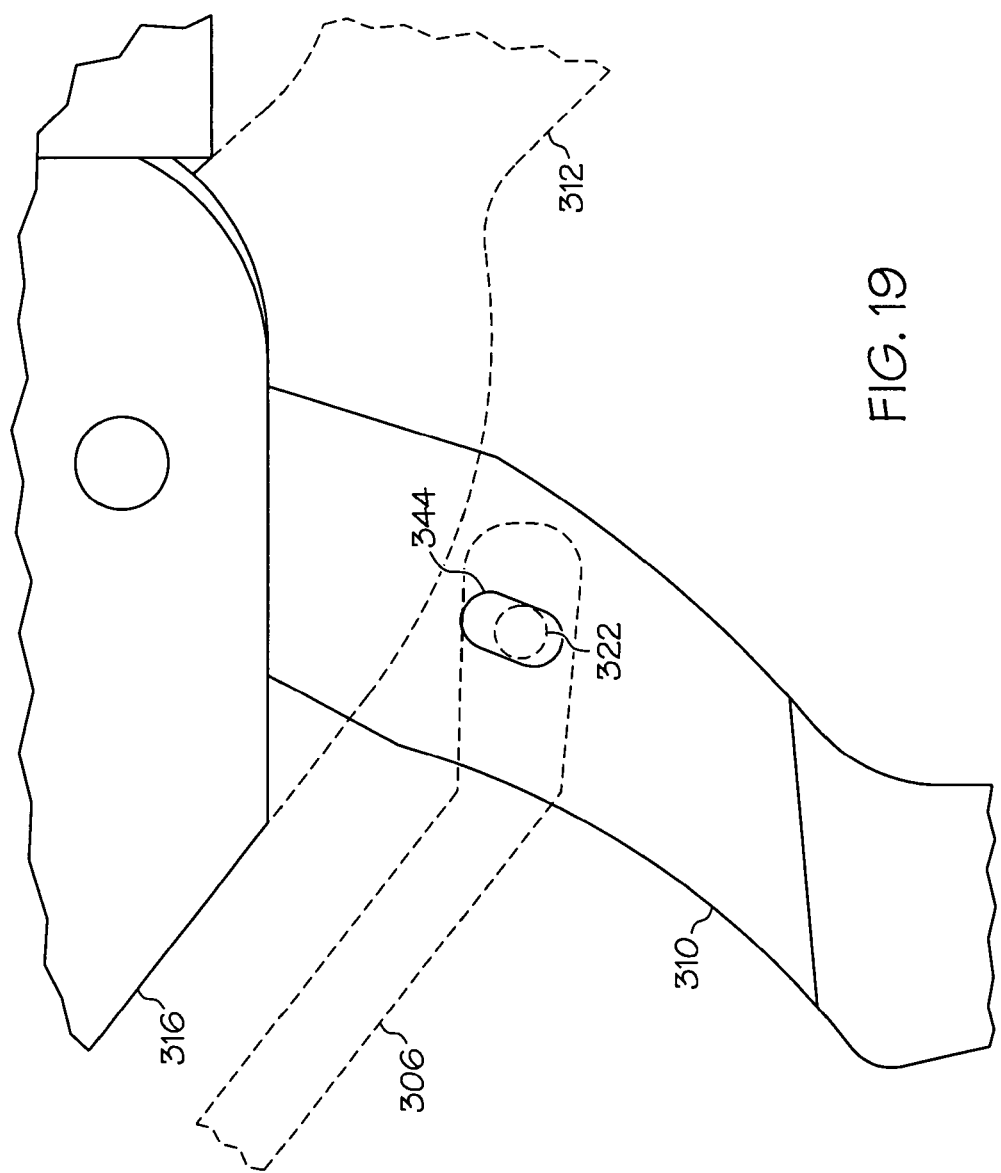
FIGS. 19-20 illustrate a handle region of one embodiment of the surgical device shown in FIG. 10.
Figure 20:
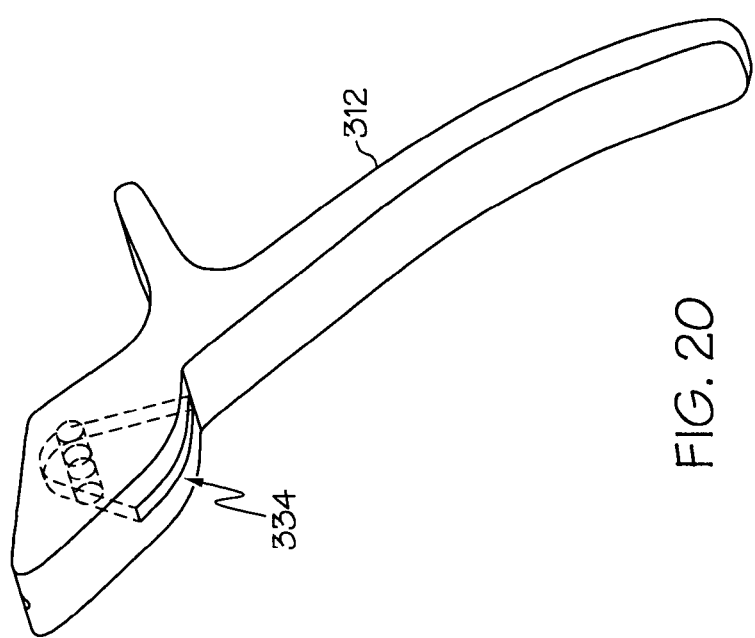

The various components of the surgical device 300 may be arranged in any suitable way. FIGS. 19-20 illustrate a handle region of one embodiment of the device 300 shown in FIG. 10. According to various embodiments, a frame member 316 may couple to the handle 312 and the trigger 310. The handle 312 may include a slot 334 for receiving the trigger 310. When the trigger 310 is positioned within the slot 334, and the frame member 316 is fitted over the handle 312 and trigger 310, the bore holes 328, 330 and 332 may align (FIGS. 11-12). Pin 320 may pass through bore holes 328, 330 and 332 to secure the frame member 316, the handle 312 and the trigger 310. The transducer assembly 302 and the end effector 304 may be received into a cavity 334 of the frame member 316. The sheath 314 may be received into a distal end of the cavity 334. A pin 318 may be placed through bore holes 340, 338 and 342 to secure the sheath 314, the end effector 304 and the frame member 316. In addition, the sheath 314 may include a tongue feature 324 that may be received into a corresponding groove feature 336 of the handle 312. (FIG. 11) FIGS. 17-18 illustrate one embodiment of a lower jaw 306 and outer sheath 314 of the surgical device 300 shown in FIG. 10, including a view of the tongue feature 324 of the sheath 314.

The lower jaw 306 may be coupled to the trigger 310 as well as the sheath 314, allowing the lower jaw 306 to translate relative to the sheath 314 and the end effector 304 when the trigger 310 is drawn toward the handle 312. For example, the lower jaw 306 may define a groove feature 326 configured to receive the tongue feature 324 of the sheath (FIGS. 17-18). A proximal end 348 of the lower jaw 306 may define one or more bore holes 346. The bore hole(s) 346 may be aligned with a slot 344 of the trigger 312, allowing pin 322 to be inserted. As illustrated in FIG. 19, the trigger 310 may pivot toward the handle 312 about pin 320. This may cause the pin 322 to slide within the slot 344, exerting a proximally directed force on the lower jaw 306 and causing the clamp face 308 to translate toward the blade 304' of the end effector 304.

Figure 20A:
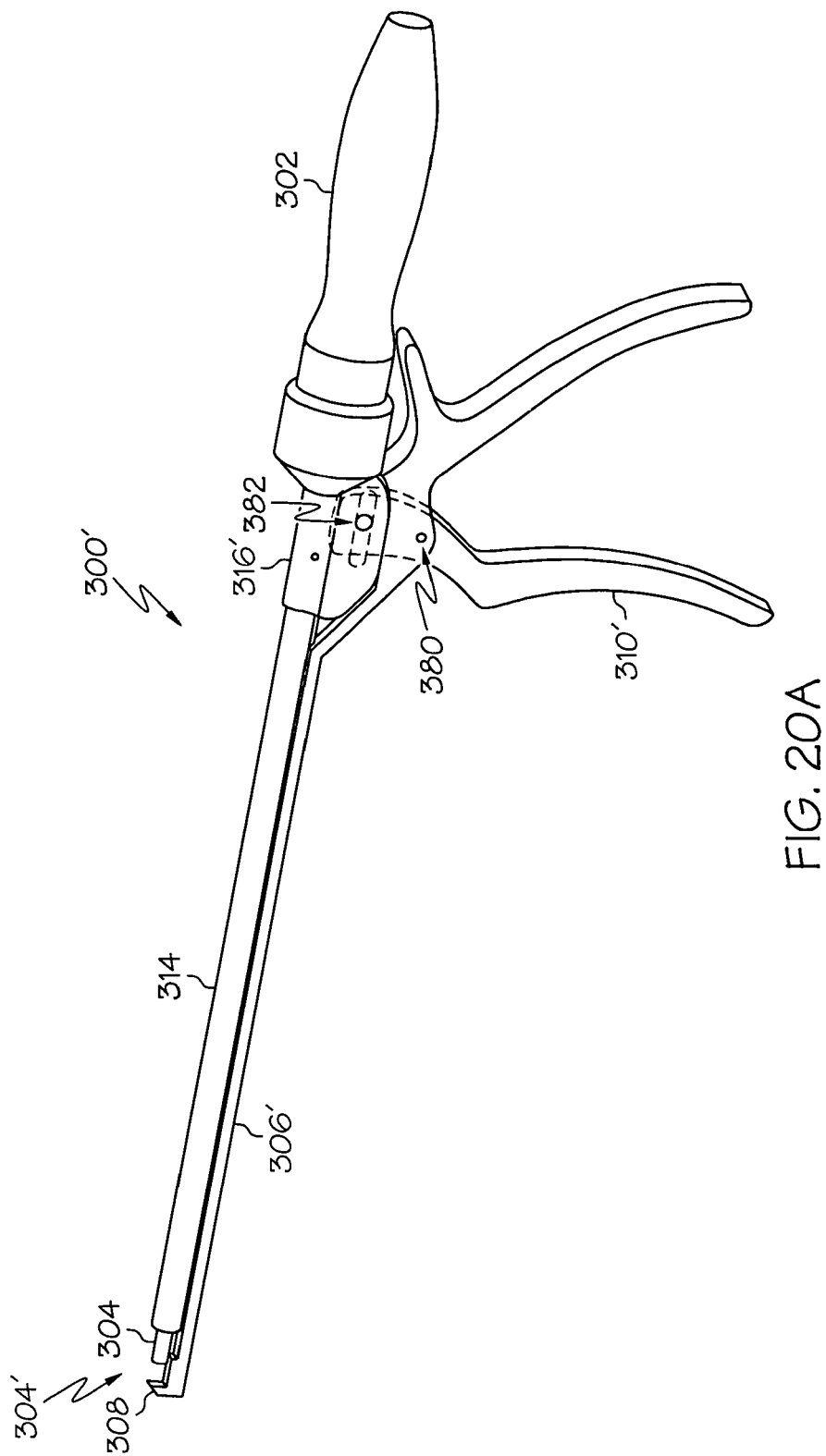
FIG. 20A illustrates one embodiment of the surgical device shown in FIG. 10.

In the embodiments described above, the lower jaw 306 is slidable while the end effector 304 remains stationary. FIG. 20A illustrates one embodiment of a surgical device 300' where the lower jaw is stationary and the end effector is slidable. A frame member 316' may couple the transducer 302, sheath 314 and end effector 304. A trigger 310' may couple to a consolidated handle/lower jaw member 306' at pivot point 380, and to the frame member 316' at pivot point 382. According to various embodiments, the pivot points 380 and 382 may comprise a pin and slot, as described above. In use, the clinician may pull the trigger 310' toward the proximal portion of the handle/lower jaw member 306'. This may cause the trigger 310' to rotate about the pivot point 380 and exert a distal force on the frame member 316', transducer 302 and end effector 304, pushing the blade 304' of the end effector distally toward the clamp face 308.

FIG. 20B illustrates one embodiment of the surgical device 300' where the end effector 304 is configured to rotate as it moves forward toward the clamp face 308. The frame member 316' may include slots 390. The end effector 304 may include a pin 392, which may be received by the slots 390. As the end effector 304 is moved distally, as described above, the orientation of the slots 392 may exert a torque on the pint 392, and consequently the end effector 304, causing it to rotate as shown. In various embodiments, the pin 392 may be replaced with multiple pins (not shown). For example, one pin may be placed on a first side of the end effector 304 and may be received by a first slot 390, while another pin may be placed on a second side of the end effector 304 and may be received by a second slot 390 opposite the first.

Figure 21:
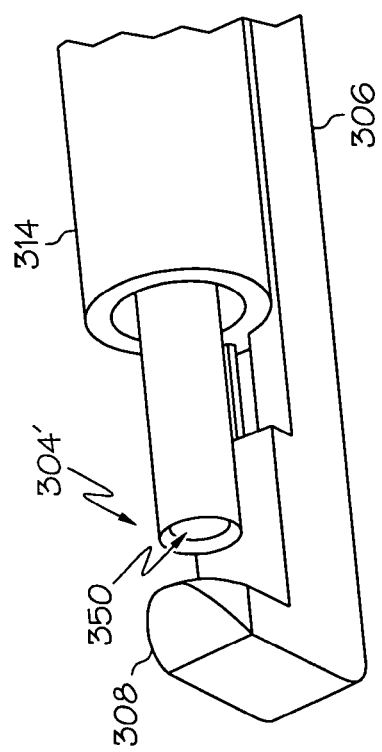
FIG. 21 illustrates a distal portion of one embodiment of the surgical device shown in FIG. 10 including a blade defining a hollow lumen.
Figure 22:
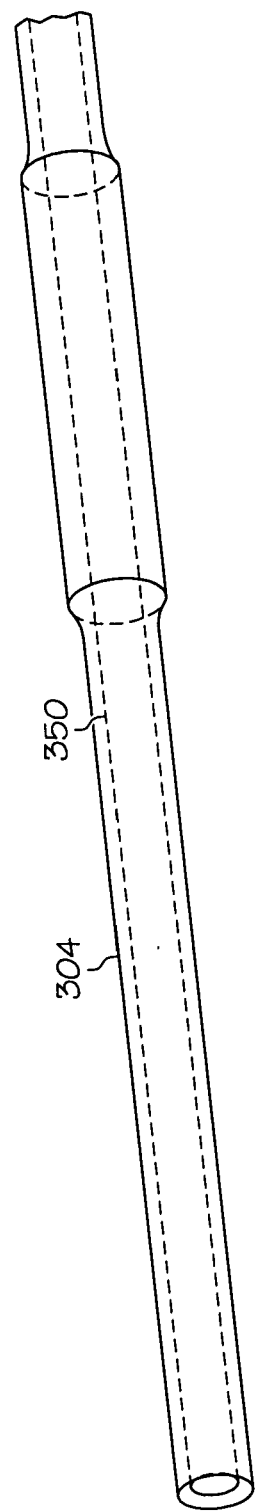
FIG. 22 illustrates one embodiment of the blade shown in FIG. 21.
Figure 23:
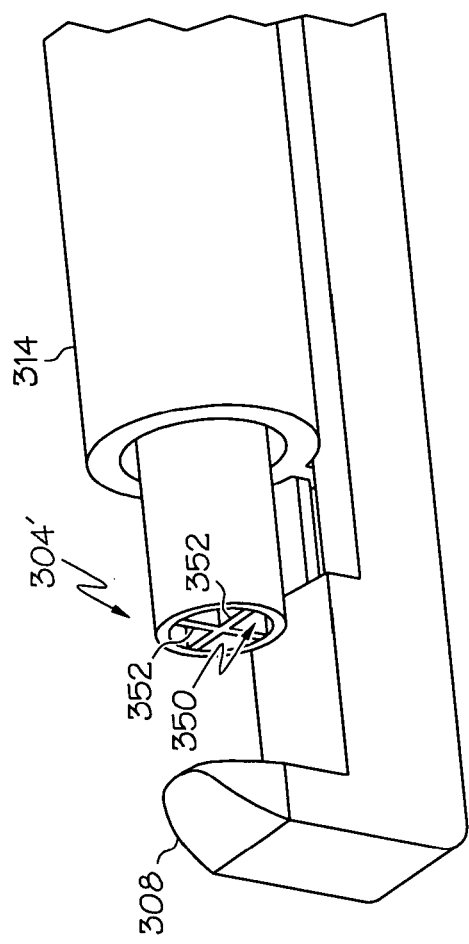
FIG. 23 illustrates a distal portion of one embodiment of the surgical device shown in FIG. 10 including a blade defining a hollow lumen and having members extending across the hollow lumen.
Figure 24:
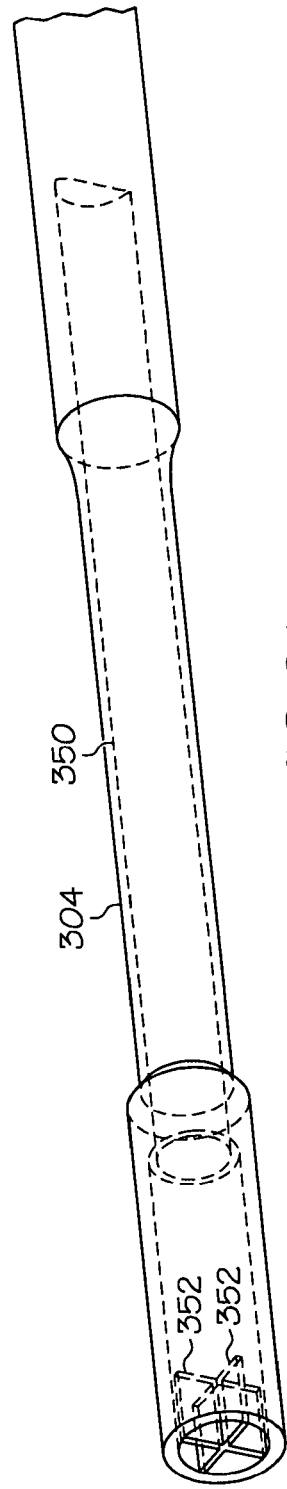
FIG. 24 illustrates one embodiment of the blade shown in FIG. 23.

The end effector 304 and the blade 304' may be constructed according to any suitable solid or hollow-core configuration. FIG. 21 illustrates a distal portion of one embodiment of the surgical device shown in FIG. 10 including a blade 304' defining a hollow lumen 350. FIG. 22 illustrates one embodiment of the blade 304' shown in FIG. 21. According to various embodiments, suction may be provided through the lumen 350 to aspirate tissue that is cut and coagulated by the end effector 304. FIG. 23 illustrates a distal portion of one embodiment of the surgical device 300 shown in FIG. 10 including a blade 304' defining a hollow lumen 350 and having two members 352 extending across the hollow lumen 350. FIG. 24 illustrates one embodiment of the blade 304' shown in FIG. 21. The members 352 may serve to cut tissue into portions smaller than the diameter of the lumen 350, thus lessening the risk of clogging the lumen 350. Various embodiments may include more or fewer members 352 than are shown. Also, the members 352 are shown to intersect one another at a right angle, although any other suitable configuration may be used.

Figure 25:
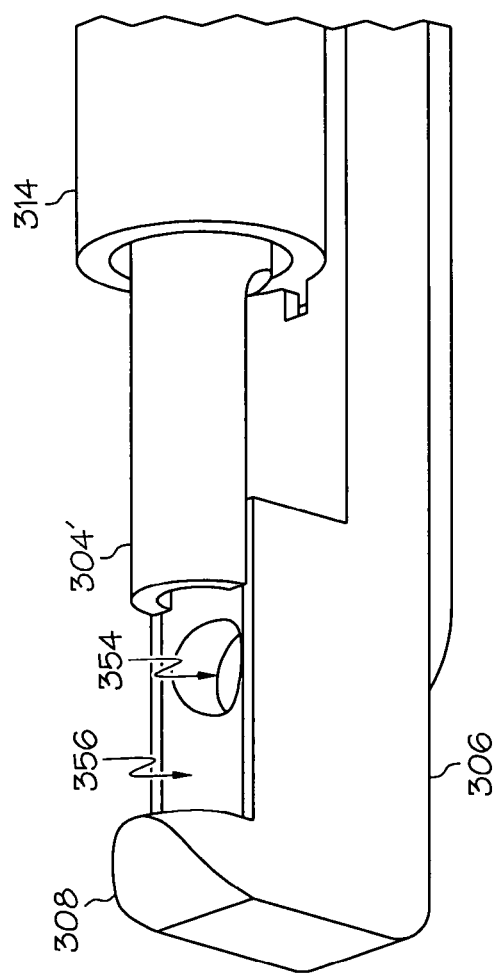
FIG. 25 illustrates a distal portion of one embodiment of the surgical device shown in FIG. 10 including a jaw member defining a lumen.
Figure 26:
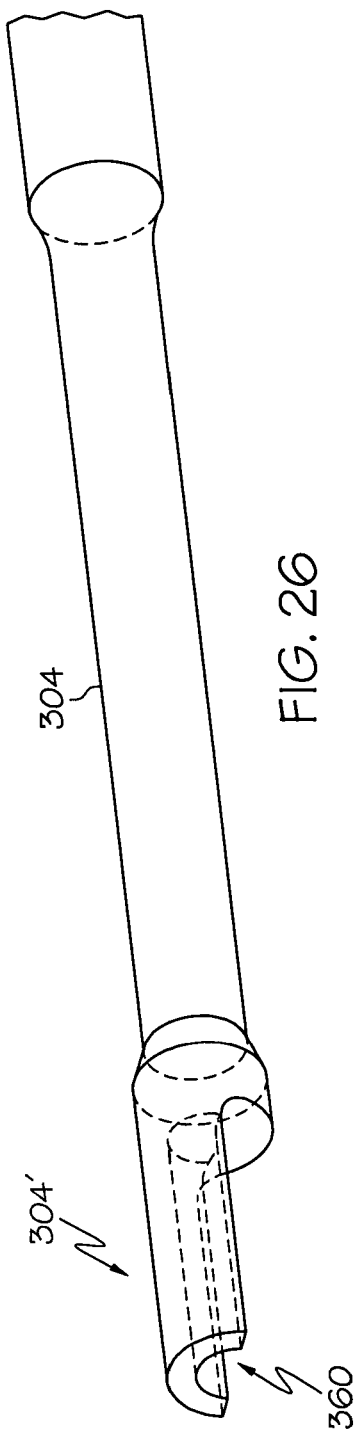
FIG. 26 illustrates one embodiment of a blade for use with the surgical device as shown in FIG. 25.
Figure 26A:
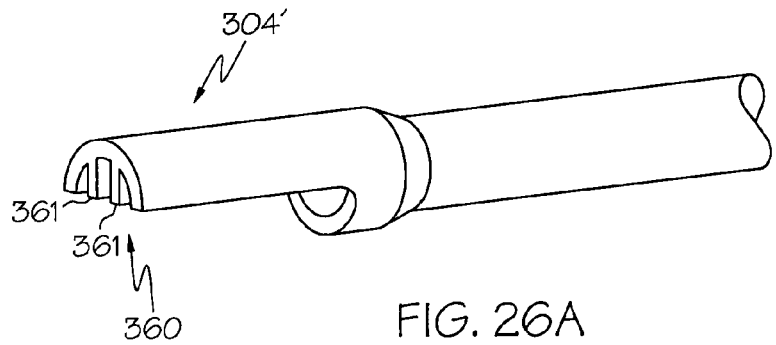
FIG. 26A illustrates an additional embodiment of the blade of FIG. 26 having cutting members positioned within a cavity of the blade.
Figure 27:
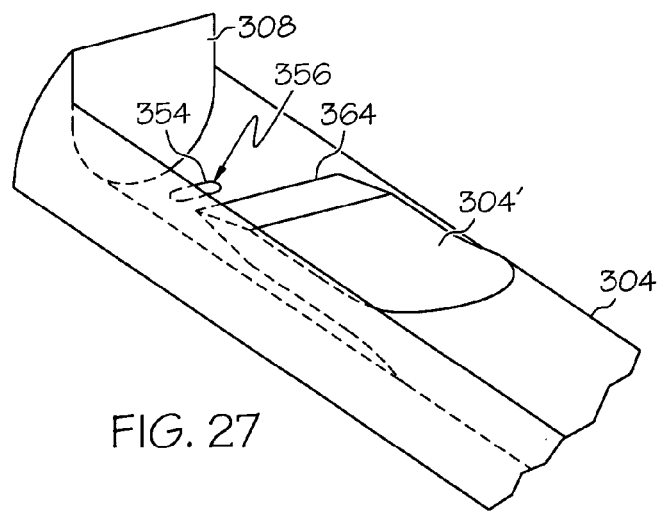
FIG. 27 illustrates a distal portion of one embodiment of the surgical device shown in FIG. 10.

FIG. 25 illustrates a distal portion of one embodiment of the surgical device 300 shown in FIG. 10 including a jaw member 306 defining a lumen, while FIG. 26 illustrates one embodiment of a blade 304' for use with the surgical device as shown in FIG. 25. The blade 304' of the end effector 304 may define a cavity 360. When the clamp face 308 is brought toward the blade 304', the cavity 360 may cover a corresponding well 356 defined by the lower jaw 306. They well 356 may define an opening 354 to a lumen located within the lower jaw 306. Tissue cut and or coagulated by the end effector 304 may be aspirated via the lumen and its opening 354. FIG. 26A illustrates an additional embodiment of the blade 304' having cutting members 361 positioned within the cavity 360. In use, the cutting members may morcellate tissue, reducing the size of tissue pieces received into the opening 354 and lessening the risk that the lumen will clog. FIG. 27 illustrates a distal portion of one embodiment of the surgical device shown in FIG. 10. In the embodiment shown in FIG. 27, the end effector 304 may include a blade 304' defining a sharp edge 364. The blade 304' may cover the well 356 and lumen opening 354 as described above.

Figure 28:
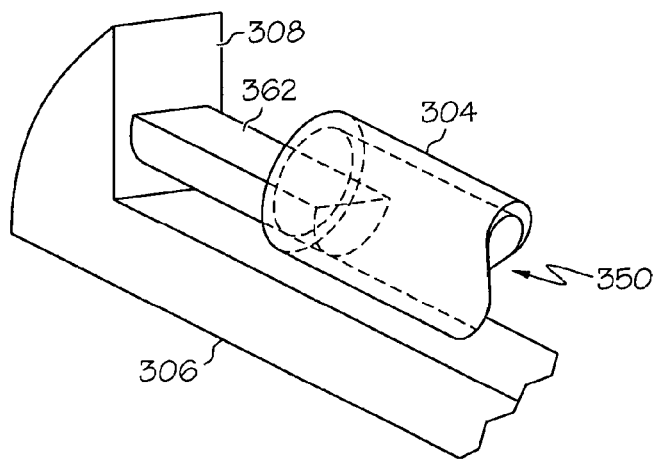
FIG. 28 illustrates a distal portion of one embodiment of the surgical device shown in FIG. 10 including a plug feature received into a hollow lumen of the end effector.

FIG. 28 illustrates a distal portion of one embodiment of the surgical device 300 shown in FIG. 10 including a plug feature 362 received into a hollow lumen 350 of the end effector 304. When the clamp face 308 is brought toward the end effector 304, the plug feature 362 may be received into a lumen 350 defined by the end effector 304. In this way, the plug feature may help to remove any clogs or blockages present within the lumen 350. According to various embodiments, the plug feature 362 may have a cross sectional area smaller than that of the lumen 350. This may generally limit tissue portions removed by the device 300 to sizes smaller than the diameter of the lumen 350, reducing the likelihood of clogs.

FIG. 28A illustrates one embodiment of the surgical device 300 including a rotating end effector 370. The rotating end effector 370 may mount to an electric motor 372. FIG. 28B illustrates one embodiment of the electric motor 372 mounted to the end effector 370. A rotor 376 of the motor 372 may be mounted around the end effector 370. A coil 374 of the motor 372 may, when energized, cause the rotor 376 and end effector 370 to rotate clockwise or counter-clockwise. In use, the lower jaw 306 may be translated with respect to the end effector 370, causing the clamp face 308 to translate toward a blade 370' of the rotating end effector 370. According to various embodiments, the embodiment shown in FIGS. 28A and 28B also may include a transducer (not shown in FIGS. 28A and 28B) for ultrasonically exciting the end effector 370. Accordingly, the end effector 370 may be rotated and ultrasonically excited simultaneously. Also, FIG. 28A illustrates a clamp pad 377 positioned between the clamp face 308 and the blade 370'. The clamp pad 377 may be made from any suitable material including, for example, a polymeric material.

Figure 28C:
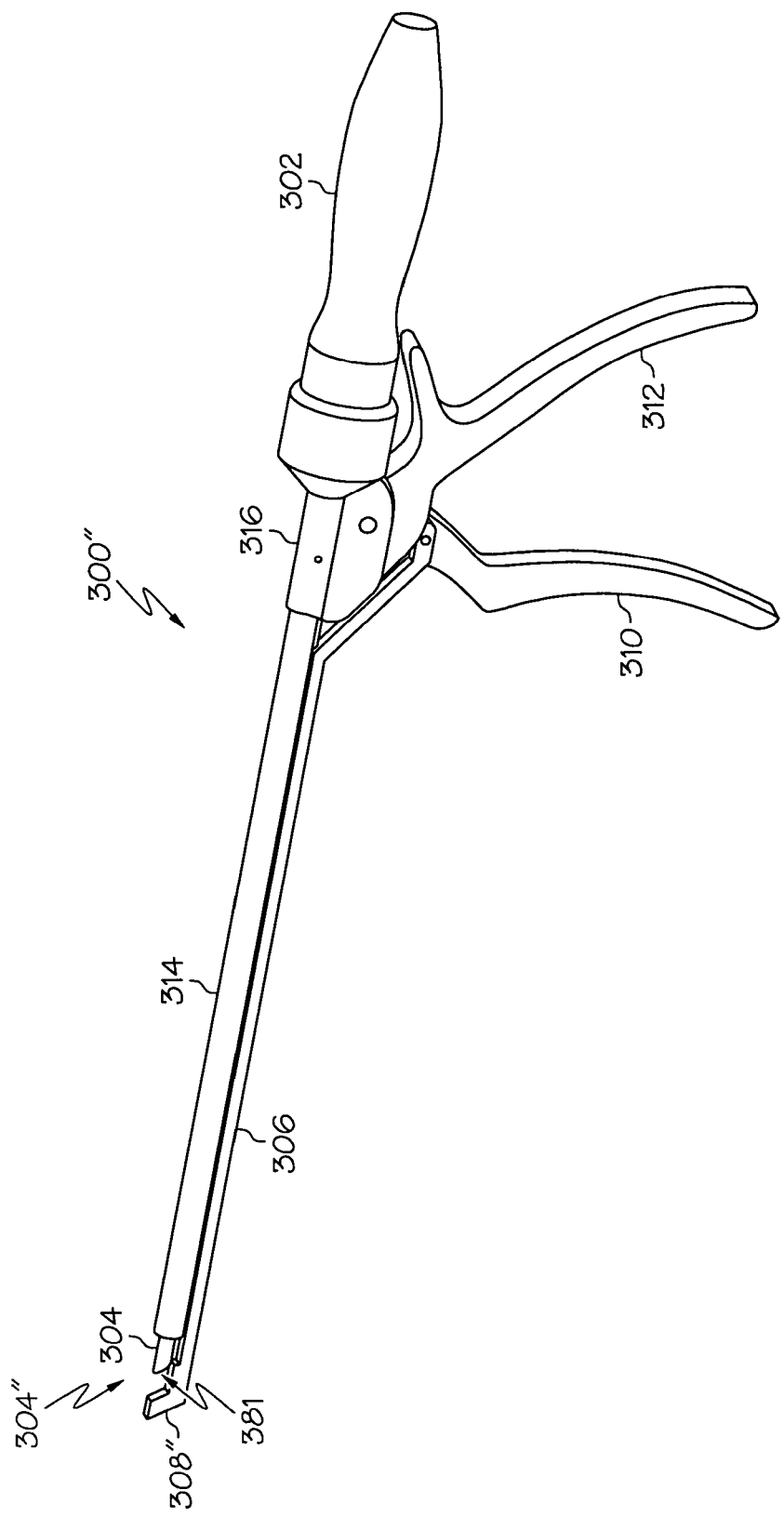
FIG. 28C illustrates one embodiment of the surgical device of FIG. 28A having an angled blade.

FIG. 28C illustrates one embodiment of the surgical device 300" having an angled blade 304". The lower jaw 306 and clamp face 308" may slide relative to the end effector 304 and blade 304" according to any suitable method including, for example, the methods described above with respect to FIGS. 10, 20A, and 20B. The blade 304" may have a distal surface 381 that is angled relative to the device 300". For example, the distal surface 381 of the blade 304" may be angled at an angle of 45°. According to various embodiments, the clamp face 308" may also be angled, as shown, to match the angle of the blade 304".

FIGS. 29-36 show various embodiments of hollow core end effectors that may be utilized to cut and/or coagulate tissue. The end effectors may define a central lumen and may comprise at least one member extended across at least a portion of the central lumen at a distal end of the end effector. The member or members may serve to break-up bone or other tissue before it passes through the lumen, making it less likely that the lumen will be clogged by tissue material. According to various embodiments, the end effectors may be utilized with any suitable manual or ultrasonic instrument. For example, the end effectors may be utilized with the surgical devices 10, 250 and 300 described above.

Figure 29:
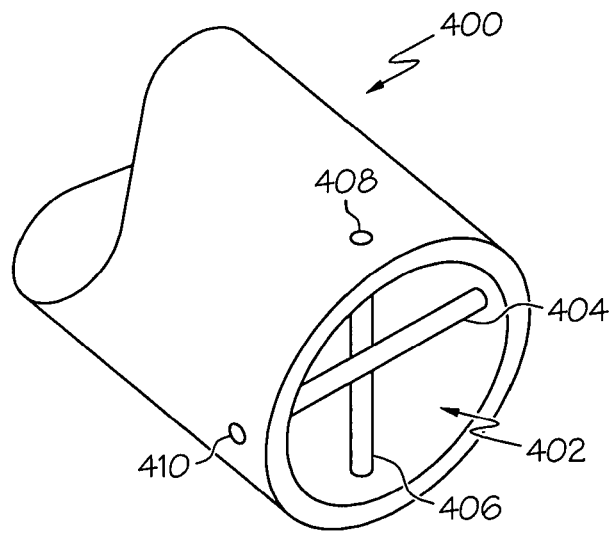
FIG. 29 illustrates one embodiment of a hollow core end effector comprising members extending across a lumen.
Figure 30:
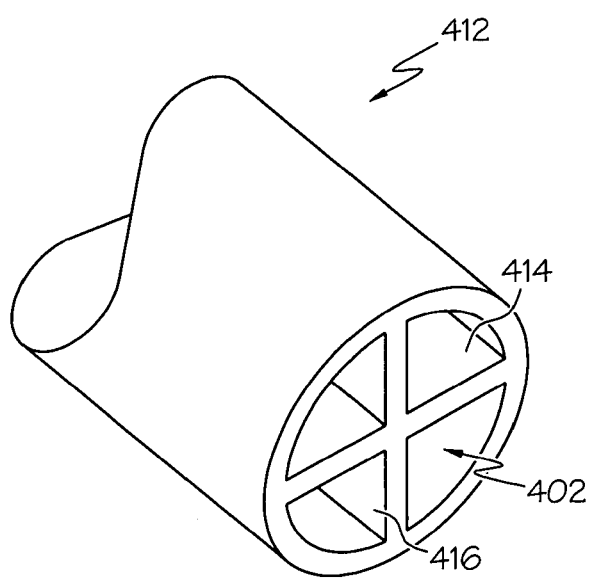
FIG. 30 illustrates one embodiment of a hollow core end effector comprising members extending across a lumen.
Figure 31:
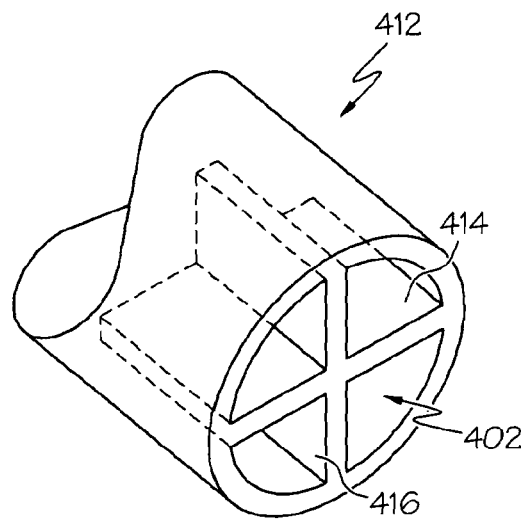
FIG. 31 illustrates a cut away view of one embodiment of the hollow core end effector shown in FIG. 30.
Figure 31A:
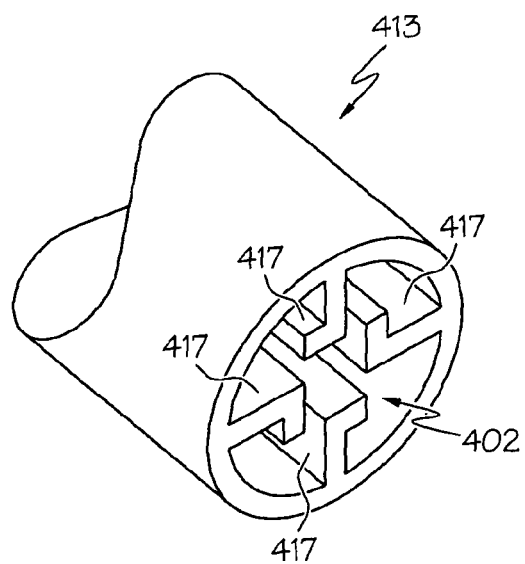
FIG. 31A illustrates one embodiment of a hollow core end effector having angled members.

FIG. 29 illustrates one embodiment of a hollow core end effector 400 comprising members 404, 406 extending across a lumen 402 defined by the end effector 400. The members 404 and 406 may comprise wires that may be bonded to the end effector 400 at various points including points 408 and 410. The wires may be bonded to the end effector 400 according to any suitable method including, welding, adhesive, etc. Also, although the embodiment shown in FIG. 29 includes two members 404 and 406 intersecting at about the center of the lumen 402, it will be appreciated that any other suitable configuration or number of members may be utilized. FIG. 30 illustrates one embodiment of a hollow core end effector 412 comprising members 414, 416 extending across a lumen 402, while FIG. 31 illustrates a cut away view of one embodiment of the hollow core end effector 412 shown in FIG. 30. In the embodiment shown in FIGS. 30-31, the members 414 and 416 may be machined into the end effector 412 itself. Accordingly, portions of the members 414, 416 may extend proximally into the lumen 402. FIG. 31A illustrates one embodiment of a hollow core end effector 413 having angled members 417. The members 417 may not extend across the lumen 402. Instead, some or all of the angled members 417 may terminate in a central portion of the lumen 402.

Figure 32:
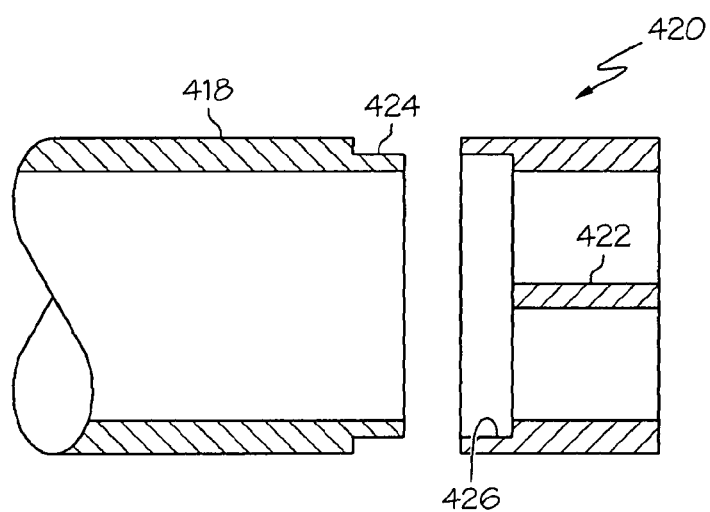
FIG. 32 illustrates one embodiment of an end effector having a non-integral blade.

FIG. 32 illustrates one embodiment of an end effector 418 having a non-integral blade 420. The blade 420 may include one or more members 422, for example, as described above with respect to end effectors 400 and 412. The blade 420 may be bonded to the remainder of the end effector 418 according to any suitable method. For example, the surfaces 424 and 426 may be threaded, allowing the blade 420 to be threaded onto the remainder of the end effector 418. Also, the blade 420 and end effector 418 may be coupled by press fitting, welding, brazing, adhesive bonding, etc. According to various embodiments, the non-integral blade 420 and the remainder of the end effector 418 may be made from different materials. For example, the end effector 418 may be made from a titanium alloy or other material with a low resistance to ultrasonic wave transmission. The blade 420 may be, in turn, made from material that is easily machined, and/or holds an edge such as, for example, a steel.

Figure 33:
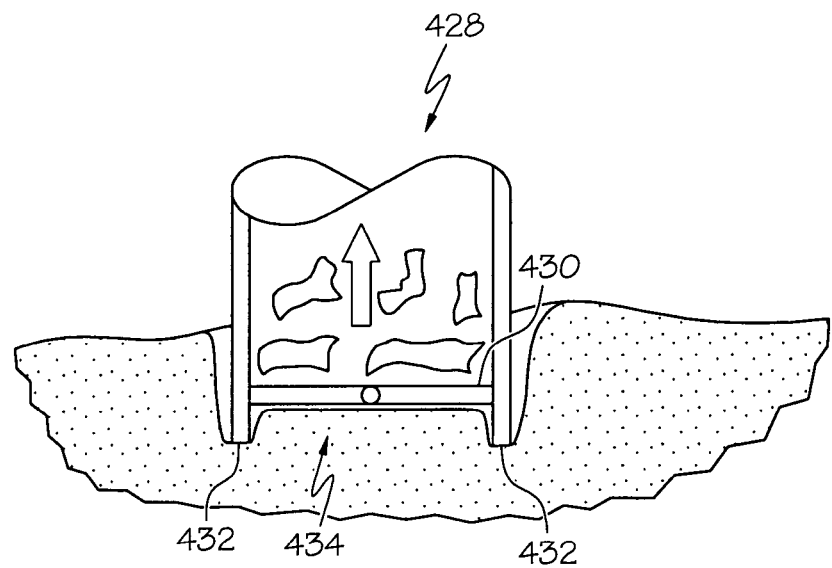
FIG. 33 illustrates one embodiment of an end effector having a member extended across a lumen and edges extending beyond the member.
Figure 34:
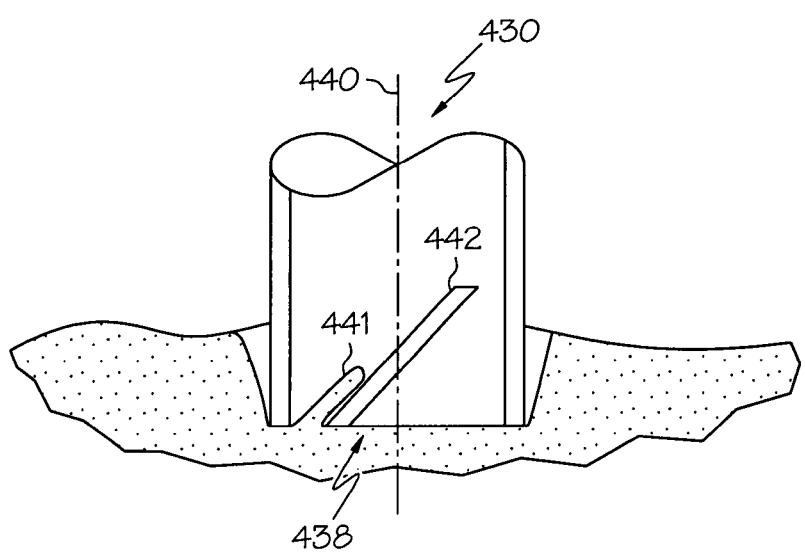
FIG. 34 illustrates one embodiment of an end effector having an inter-lumen member positioned non-parallel to a longitudinal axis of the end effector.
Figure 35:
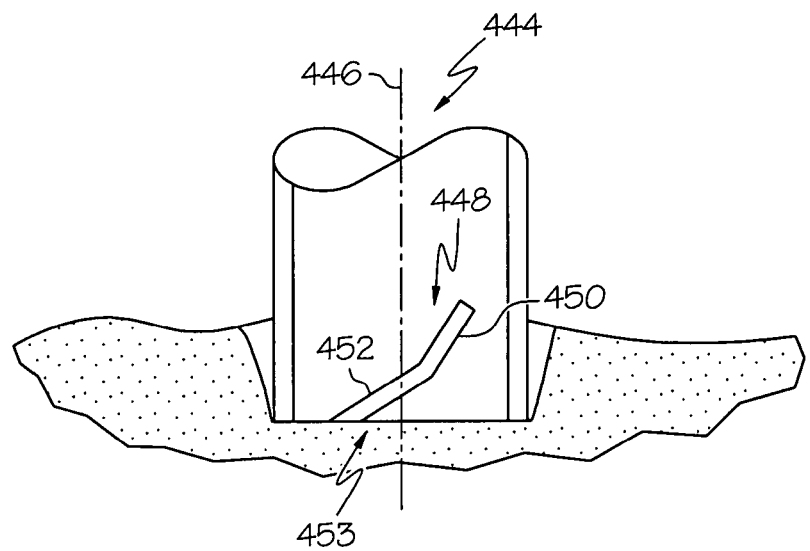
FIG. 35 illustrates one embodiment of an end effector having a multi-section inter-lumen member.
Figure 36:
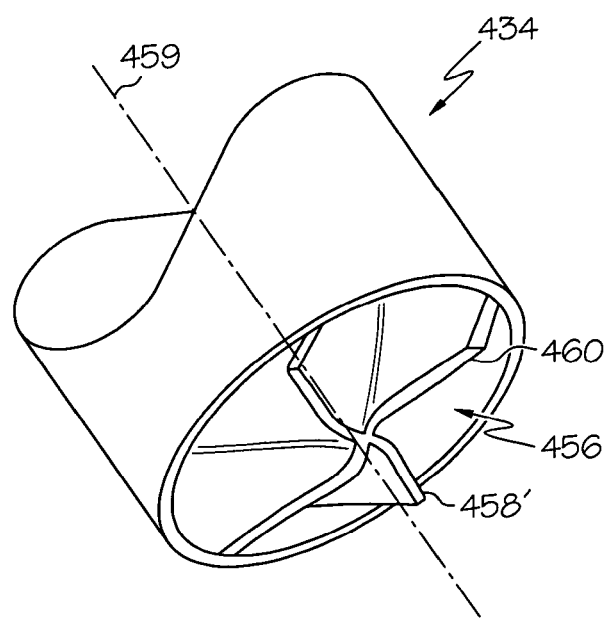
FIG. 36 illustrates one embodiment of an end effector having inter-lumen members extending distally.

FIG. 33 illustrates one embodiment of an end effector 428 having a member 430 extended across a lumen 434 and edges 432 extending beyond the member 430. The member 430, as shown, is positioned proximally from the distal edge of the end effector 428. For example, the member 430 may be recessed within the lumen 434 by a distance of up to 15 mm. FIG. 34 illustrates one embodiment of an end effector 436 having an inter-lumen member 442 positioned non-parallel to a longitudinal axis 440 of the end effector 436. The member 442 may extend proximally into the lumen 438 at an angle that is not parallel to the axis 440. This may facilitate the cutting and removing of small portions of tissue, such as tissue portion 441. FIG. 35 illustrates one embodiment of an end effector 444 having a multi-section inter-lumen member 448. Each of the sections 450, 452 of the inter-lumen member 448 may be positioned at different angles relative to the longitudinal axis 446. FIG. 36 illustrates one embodiment of an end effector 454 having inter-lumen members 458, 460 extending distally from the lumen 434. The members 458, 460 may be angled relative to the longitudinal axis 459, as described above. The members 458 and 460 also may extend beyond the distal edge of the other portions of the end effector 454.

FIGS. 37-54 illustrate various embodiments of surgical devices that may be used as an ultrasonic or unpowered device to remove tissue portions. The embodiments illustrated in FIGS. 37-54 may be useful in surgical applications where it is desirable to remove a core or other integral portion of bone or other tissue. The devices may generally comprise a central instrument configured to engage tissue and an outer sheath surrounding the central instrument. The central instrument and sheath may be slidable relative to one another. Also, the outer sheath may comprise a distal edge configured to clamp the tissue when the central instrument is slid to a position proximal from the distal edge of the outer sheath.

Figure 37:
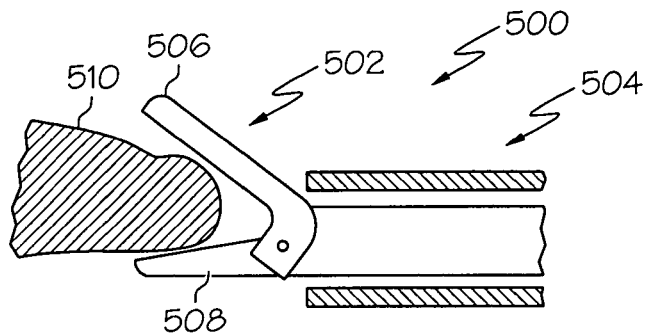
FIG. 37 illustrates one embodiment of a surgical device comprising a central instrument and an outer sheath.
Figure 38:
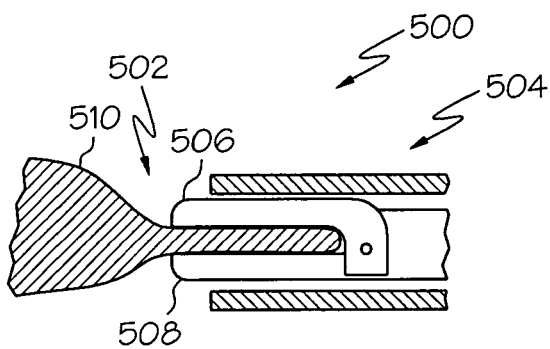
FIG. 38 illustrates one embodiment of the surgical device shown in FIG. 37 where the central instrument is grasping tissue.
Figure 39:
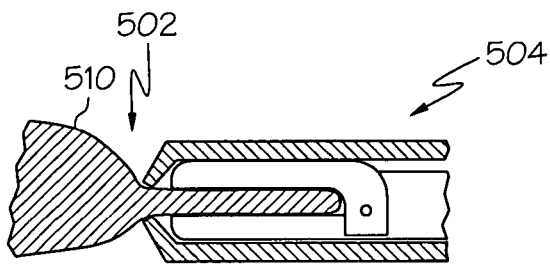
FIG. 39 illustrates one embodiment of the surgical device shown in FIG. 37 where the outer sheath has clamped the tissue.
Figure 40:
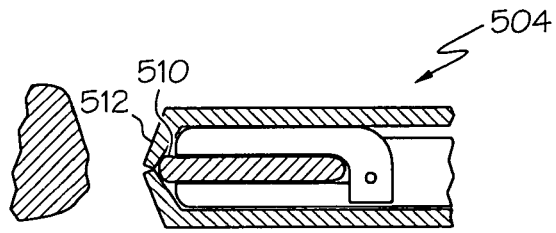
FIG. 40 illustrates one embodiment of the surgical device shown in FIG. 37 where the tissue has been severed.

FIGS. 37-40 illustrate a sequence of one embodiment of a surgical device 500 in use. The surgical device 500 may comprise a central instrument 502 and an outer sheath 504. The central instrument 502 comprises two jaw members 506 and 508. In use, the jaw member 506 may be pivotable toward the jaw member 508. According to various embodiments, the jaw member 508 may be ultrasonically energized, for example, as described above. FIG. 37 illustrates one embodiment of the surgical device 500 with a portion of tissue 510 positioned between the jaw members 506, 508. FIG. 38 illustrates one embodiment of the surgical device 500 shown in FIG. 37 where the central instrument 502 is grasping tissue. This may occur when the jaw members 506, 508 are pivoted toward one another to engage the tissue 510. In the embodiment shown in FIG. 38, the outer sheath 504 has been moved distally relative to the central instrument 502. FIG. 39 illustrates one embodiment of the surgical device 500 shown in FIG. 37 where the outer sheath 504 has clamped the tissue 510. This may occur when a distal portion of the outer sheath 504 clears the distal edge of the central instrument 502, allowing the outer sheath 504, and/or a component thereof, to clamp the tissue 510. According to various embodiments, a distal edge 512 of the outer sheath 504 may define a sharp edge to sever the tissue. Also, according to various embodiments, outer sheath 504 may be ultrasonically activated to promote cutting and/or coagulation. Once the outer sheath 504 has clamped the tissue 510, a clinician may manipulate the device 500, causing the clamped tissue 510 to tear or break. FIG. 40 illustrates one embodiment of the surgical device 500 shown in FIG. 37 where the tissue 510 has been severed.

The outer sheath 504 may exert a clamping force on the tissue 510 according to various different methods. For example, the outer sheath 504 may be constructed such that the distal edge portion 512 is biased in upon itself. Accordingly, the rest state of the edge portion 512 may be a closed or clamped position, as illustrated in FIG. 40. When the central instrument 502 is extended distally through the outer sheath 504, it may separate the edge portion 512, for example, as illustrated in FIGS. 37-38. According to various embodiments, the distal edge 512 may include multiple distal edge portions separated by one or more longitudinal slots (not shown). This may allow the distal edge 512 to separate. When the central instrument 502 is retracted through the outer sheath 504 the edge portion 512 may contract to its closed or clamped position, cutting or otherwise clamping the tissue 510. According to various embodiments, the edge portion 512 of the outer sheath 504 may be ultrasonically activated to promote cutting and/or coagulation of the tissue 510.

Figure 41:
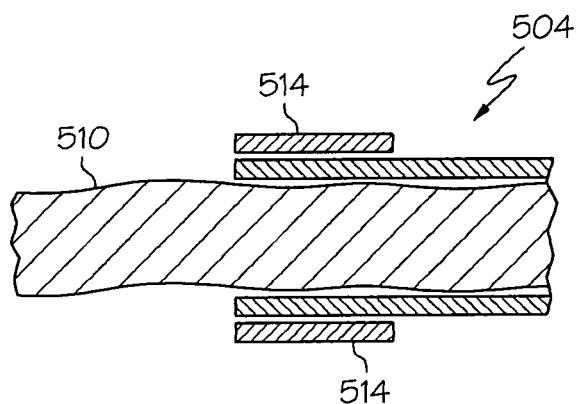
FIGS. 41-42 illustrate one embodiment of the surgical device shown in FIG. 37 where the outer sheath comprises edge members.
Figure 42:
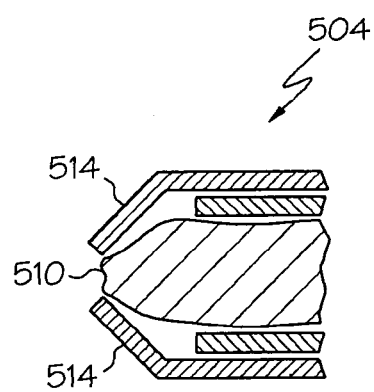

FIGS. 41-42 illustrate one embodiment of the surgical device 500 shown in FIG. 37 where the outer sheath 504 comprises edge members 514. The edge members 514 may extend distally, as shown in FIG. 41, in response to the actuation of a trigger or other component of the device (not shown). When the edge members 514 reach the distal end of the outer sheath, they contract toward one another, as shown in FIG. 42, to sever or otherwise clamp the tissue 510. According to various embodiments, the members 514 may be ultrasonically activated.

Figure 43:
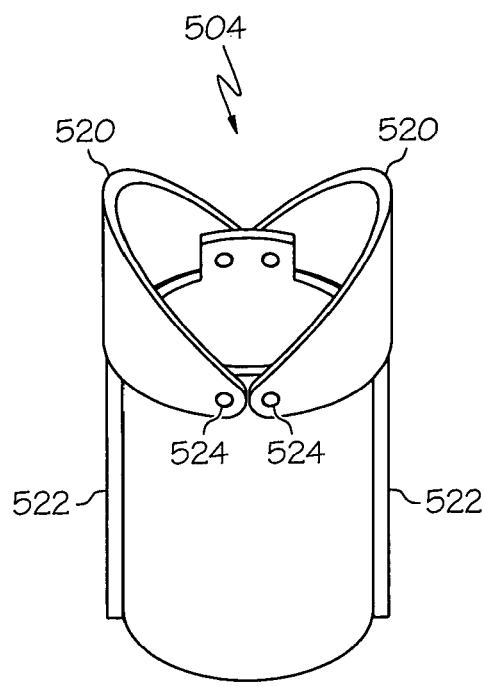
FIGS. 43 and 45 illustrate one embodiment of the outer sheath of the device shown in FIG. 37 comprising a pair of jaw members in an open position.
Figure 44:
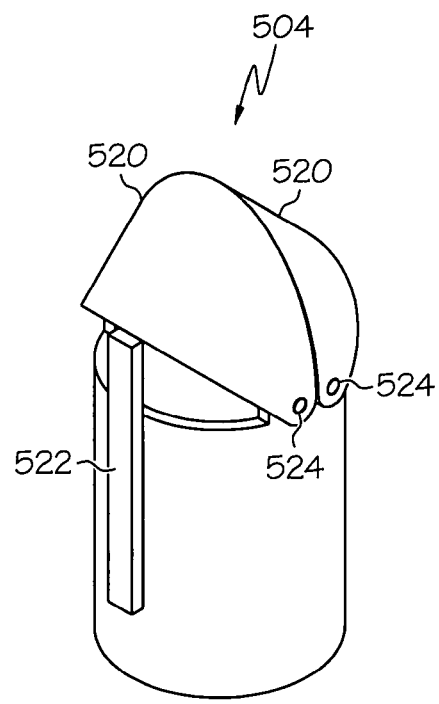
FIGS. 44 and 46 illustrate one embodiment of the outer sheath of the device shown in FIG. 37 where the jaw members are in a closed position.
Figure 46:
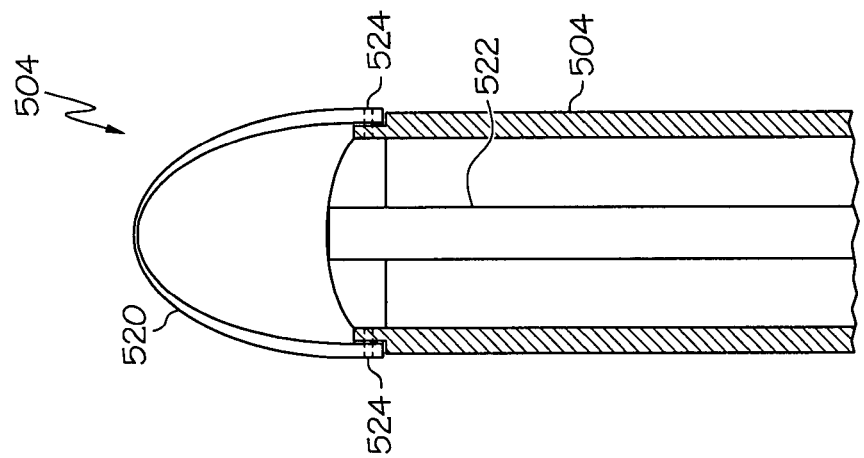
Figure 45:
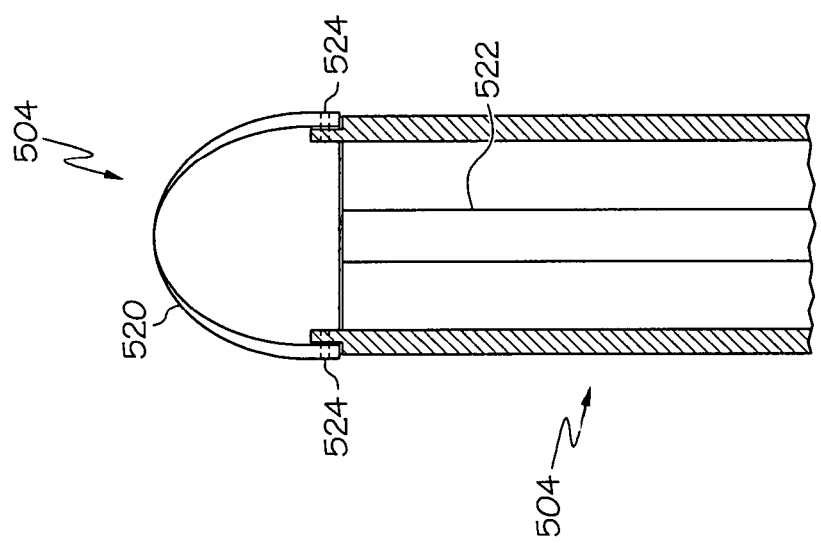

FIGS. 43-46 illustrate one embodiment of the outer sheath 504 including jaw members 520. The jaw members 520 may pivot toward one another about pivot points 524 in response to distal movement of extenders 522. For example, when the central instrument 502 is initially engaging tissue 510, as shown in FIGS. 37-38, the extenders 522 may be retracted, leaving the jaw members 520 in an open position as shown in FIGS. 43 and 45. When the outer sheath 504 is extended distally relative to the central instrument, the extenders 522 may be translated distally. Distal translation of the extenders 522 may be caused by various mechanical or automated forces, for example, in response to a clinician activating a trigger or other component of the device (not shown). This distal translation may cause the jaw members 520 to pivot about pivot points 524 to a closed position, as shown in FIGS. 44 and 46.

Figure 47:
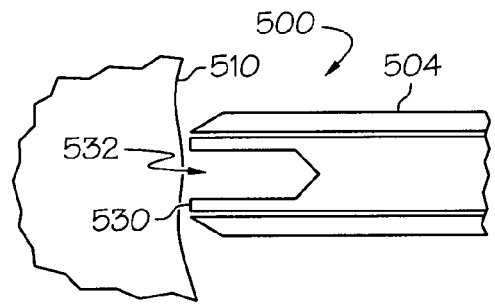
FIG. 47 illustrates one embodiment of another surgical device having a central instrument and an outer sheath.
Figure 48:
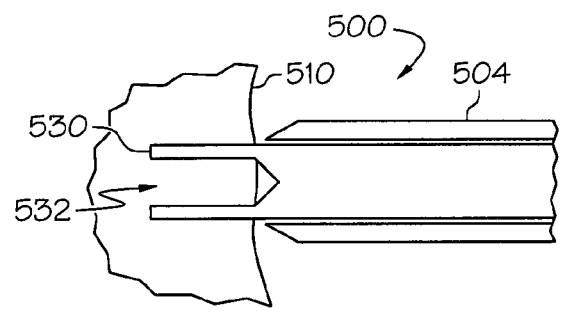
FIG. 48 illustrates one embodiment of the surgical instrument of FIG. 47 where the central instrument is extended into tissue.
Figure 49:
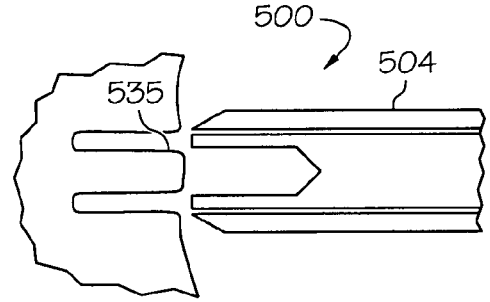
FIG. 49 illustrates one embodiment of the surgical instrument of FIG. 47 where the central instrument has been retracted from the tissue.
Figure 50:
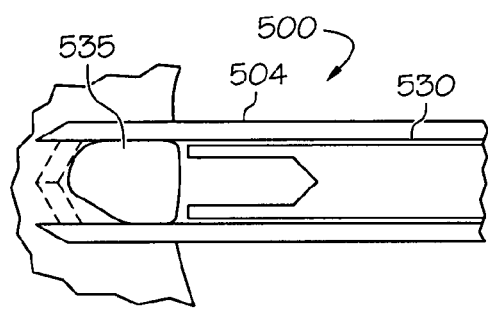
FIG. 50 illustrates one embodiment of the surgical instrument of FIG. 47 where the outer sheath has been extended into the tissue.
Figure 51:
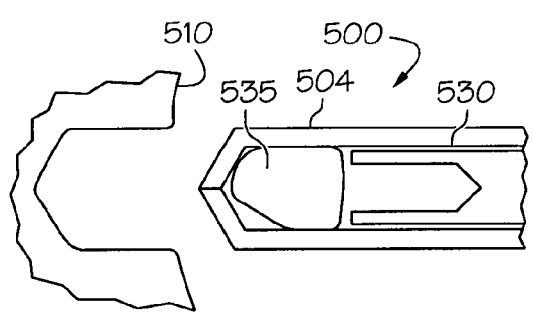
FIG. 51 illustrates one embodiment of the surgical instrument of FIG. 47 where the outer sheath has been retracted from the tissue.

FIGS. 47-51 illustrate another sequence of one embodiment of a surgical device 500 in use. The embodiment shown in FIGS. 47-51 may comprise a central instrument 530 that includes an ultrasonic end effector defining a coring cavity 532. When the central instrument 530 is extended into tissue 510, it may cut and/or coagulate around a portion of the tissue 535 corresponding to the cavity 532. FIG. 47 illustrates one embodiment of the surgical instrument 500 brought into the proximity of a mass of tissue 510. FIG. 48 illustrates one embodiment of the surgical instrument 500 of FIG. 47 where the central instrument 530 is extended into the tissue 510. Ultrasonic energy may be provided to the central instrument 530, allowing it to cut into the tissue 510. FIG. 49 illustrates one embodiment of the surgical instrument 500 of FIG. 47 where the central instrument 530 has been retracted from the tissue 510, leaving a core section 535 that has been partially severed from the tissue 510. FIG. 50 illustrates one embodiment of the surgical instrument 500 of FIG. 47 where the outer sheath 504 has been extended into the tissue 510. The outer sheath 504 may either sever the core section 535, or clamp it, allowing the clinician to tear or otherwise loosen the core section 535. FIG. 51 illustrates one embodiment of the surgical instrument 500 of FIG. 47 where the outer sheath 504 has been retracted from the tissue 510, removing the core section 535. According to various embodiments, the device 500 may omit the central instrument 502. For example, the outer sheath 504 may be ultrasonically energized to cut a portion of the tissue 510 in a manner similar to that of the central instrument 530. The outer sheath 504 may then clamp the tissue 510 for severing or tearing, for example, as described above.

The surgical device 500 may be operated by a clinician from a handle portion (not shown) that may include one or more triggers for actuating the central instrument 502 and the outer sheath 504. For example, the central instrument 502 may be actuated by any suitable manual or automatic means including, for example, a mechanical design similar to that described above with respect to the blade 180' and clamp arm 190. The outer sheath 504 may similarly be extended and actuated by any suitable manual or automatic means. For example, the outer sheath 504 may be extended distally in response to the actuation of a trigger in a manner similar to the way that the reciprocal actuating member 170 is extended distally in response to actuation of the operating lever 222 described above. According to various embodiments, the central instrument 502 and the outer sheath 504 may be actuated by a single pull of a trigger. For example, a single trigger pull may both actuate the central instrument 502 and also subsequently extend and actuate the outer sheath 504.

FIGS. 52-55 illustrate force-feedback surgical devices, according to various embodiments, configured to apply ultrasonic energy to tissue at a variable power level and/or end effector amplitude. The level of power or end effector amplitude provided to the devices may be determined, for example, based on the force applied to a trigger, and/or the position or travel of the trigger. It will be appreciated that force feedback surgical devices, such as the embodiments shown in FIGS. 52-55, may give clinicians an increased level of control over the ultrasonic power delivered by the devices, facilitating precise operations.

Figure 52:
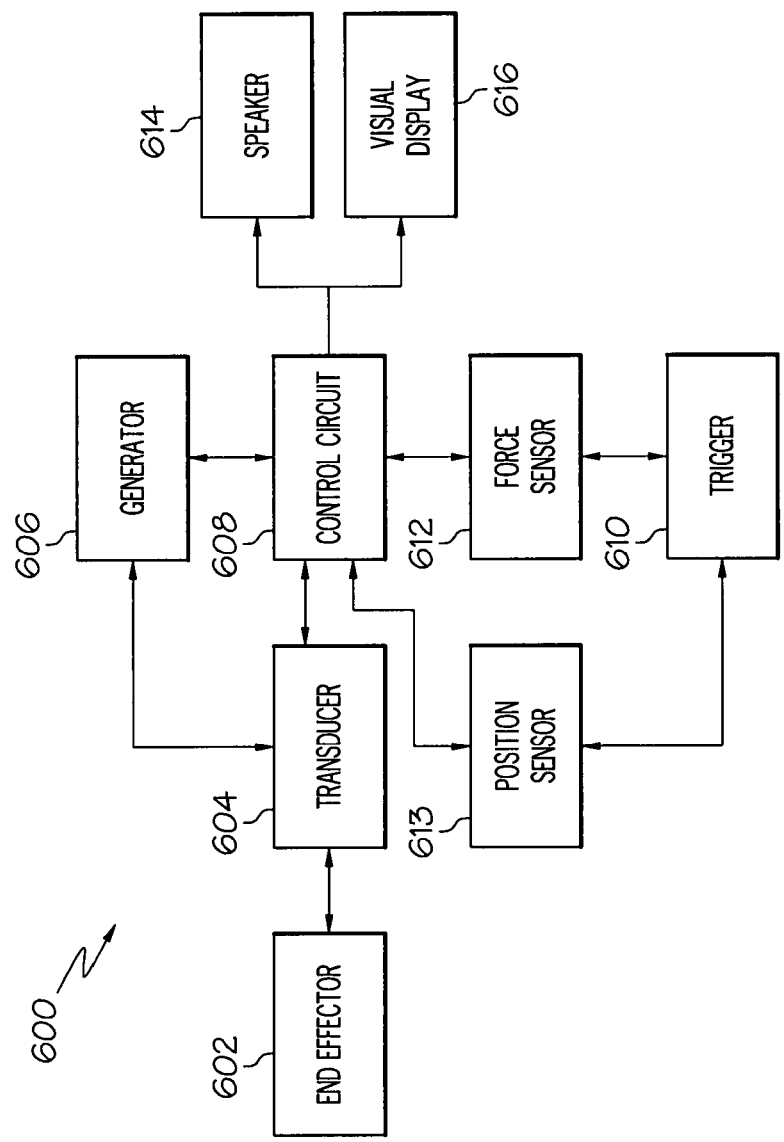
FIG. 52 illustrates a block diagram of one embodiment of a surgical device.
Figure 57:
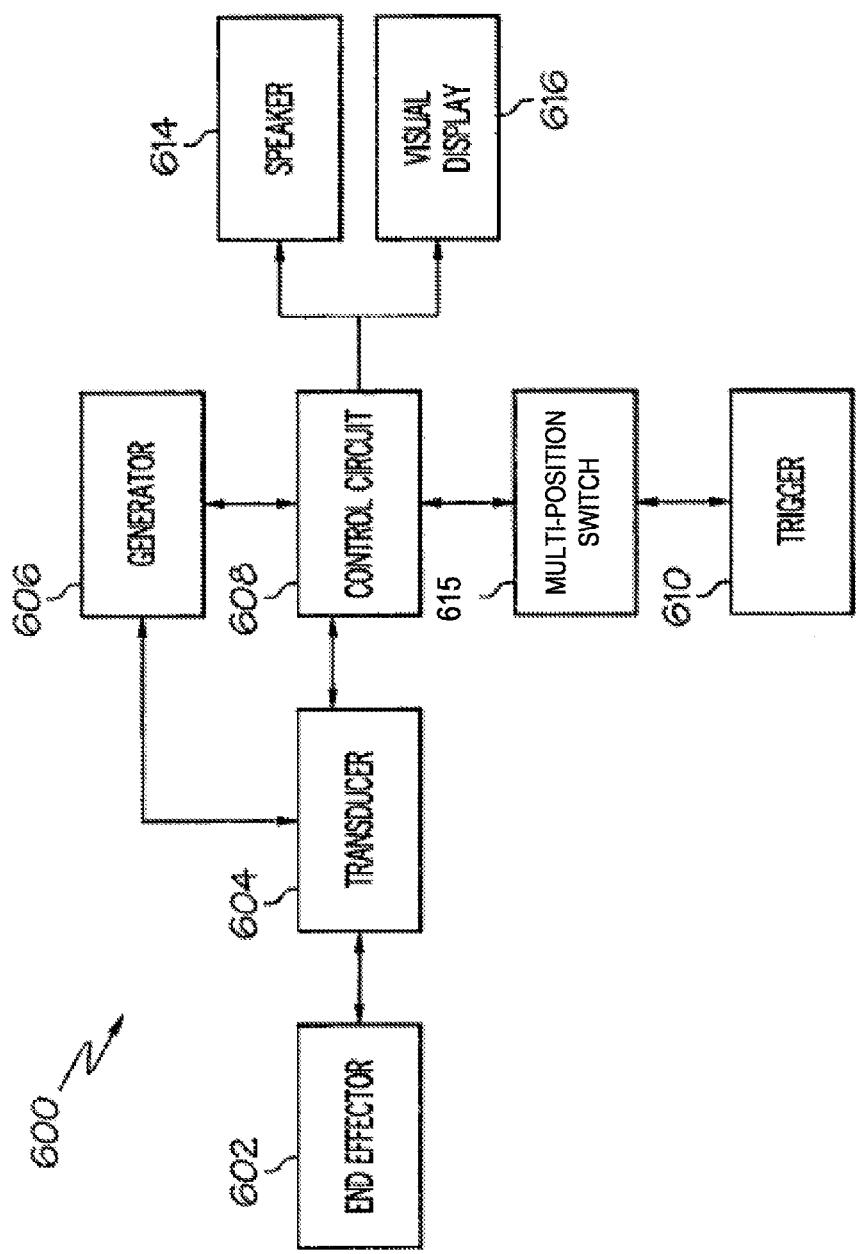
FIG. 57 illustrates a block diagram of one embodiment of a surgical device.

FIG. 52 illustrates a block diagram of one embodiment of a force feedback surgical device 600. The device 600 may include an ultrasonic end effector 602, which may be activated when a clinician operates a trigger 610. When the trigger 610 is actuated, a force sensor 612 may generate a signal indicating the amount of force being applied to the trigger 610. In addition to, or instead of force sensor 612, the device 600 may include a position sensor 613, which may generate a signal indicating the position of the trigger 610 (e.g., how far the trigger has been depressed or otherwise actuated). A control circuit 608 may receive the signals from the sensors 612 and/or 613. The control circuit 608 may include any suitable analog or digital circuit components. The control circuit 608 also may communicate with the generator 606 and/or the transducer 604 to modulate the power delivered to the end effector 602 and/or the generator level or blade amplitude of the end effector 602 based on the force applied to the trigger 610 and/or the position of the trigger 610. For example, as more force is applied to the trigger 610, more power and/or a higher blade amplitude may be delivered to the end effector 602. According to various embodiments, the force sensor 612 may be replaced by a multi-position switch. FIG. 57 illustrates a block diagram of one embodiment of the surgical device 600 of FIG. 52 where the force sensor 612 is replaced by a multi-position switch 615. Each position of the switch may correspond to a different level of power to be delivered to the end effector 602.

According to various embodiments, the end effector 602 may include a clamping mechanism, for example, such as that described above with respect to FIG. 4. When the trigger 610 is initially actuated, clamping mechanism may close, clamping tissue between a clamp arm and the end effector 602. As the force applied to the trigger increases (e.g., as sensed by force sensor 612) the control circuit 608 may increase the power delivered to the end effector 602 by the transducer 604 and/or the generator level or blade amplitude brought about in the end effector 602. In one embodiment, trigger position, as sensed by position sensor 613, may be used by the control circuit 608 to set the power and/or amplitude of the end effector 602. For example, as the trigger is moved further towards a fully actuated position, the power and/or amplitude of the end effector 602 may be increased.

According to various embodiments, the surgical device 600 also may include one or more feedback devices for indicating the amount of power delivered to the end effector 602. For example, a speaker 614 may emit a signal indicative of the end effector power. According to various embodiments, the speaker 614 may emit a series of pulse sounds, where the frequency of the sounds indicates power. In addition to, or instead of the speaker 614, the device may include a visual display 616. The visual display 616 may indicate end effector power according to any suitable method. For example, the visual display 616 may include a series of light emitting diodes (LEDs), where end effector power is indicated by the number of illuminated LEDs. The speaker 614 and/or visual display 616 may be driven by the control circuit 608. According to various embodiments, the device 600 may include a ratcheting device (not shown) connected to the trigger 610. The ratcheting device may generate an audible sound as more force is applied to the trigger 610, providing an indirect indication of end effector power.

The device 600 may include other features that may enhance safety. For example, the control circuit 608 may be configured to prevent power from being delivered to the end effector 602 in excess of a predetermined threshold. Also, the control circuit 608 may implement a delay between the time when a change in end effector power is indicated (e.g., by speaker 614 or display 616), and the time when the change in end effector power is delivered. In this way, a clinician may have ample warning that the level of ultrasonic power that is to be delivered to the end effector 602 is about to change.

Figure 53:
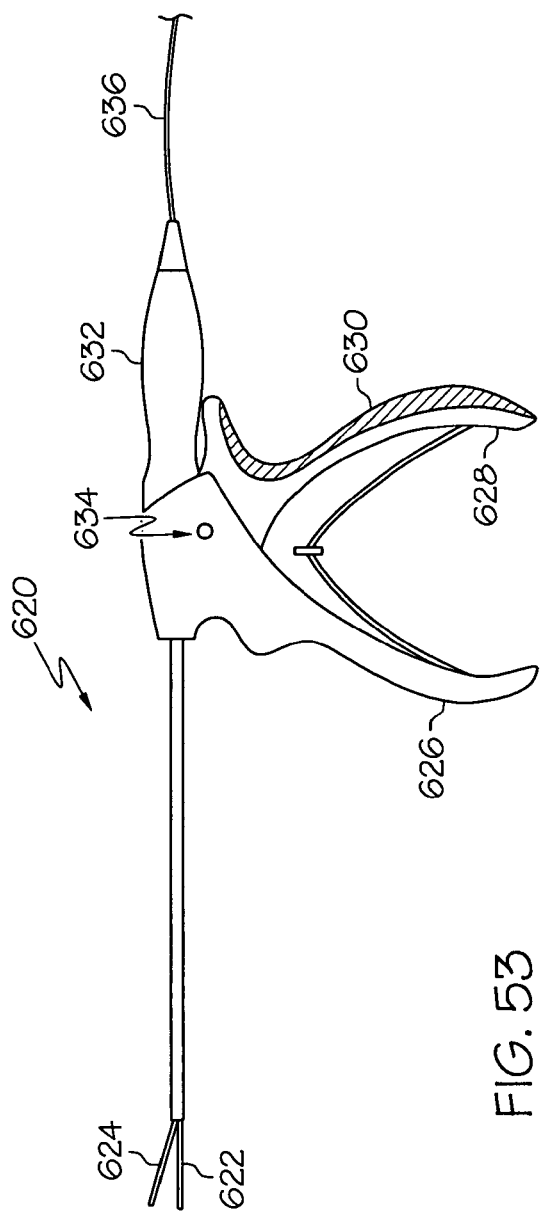
FIG. 53 illustrates one embodiment of a surgical device.

Force-feedback ultrasonic devices, such as the device 600, may be physically implemented in any suitable form. For example, FIG. 53 illustrates one embodiment of a force-feedback surgical device 620. The device 620 may comprise an ultrasonic end effector 622 excitable by a transducer 632. The transducer 632 may be in communication with a generator (not shown) via a wire 636. A clamp arm 624 may be pivotable towards the end effector 622 when a clinician pulls a trigger 628 towards a handle 626, similar to the clamp arm 190 and blade 180' described above. A sensor 630 positioned on the trigger 628 may measure the force applied to the trigger 628 by the clinician and/or the position of the trigger 628. It will be appreciated that the sensor 630 may be alternatively placed at other locations within the device 620 including, for example, at trigger pivot point 634 or between the end effector 622 and clamp arm 624. A control circuit (not shown) may be positioned at any suitable location on or in the device 620 including, for example, within the handle 626 or trigger 628, the ultrasonic drive unit 50 or the generator 30.

Figure 54:
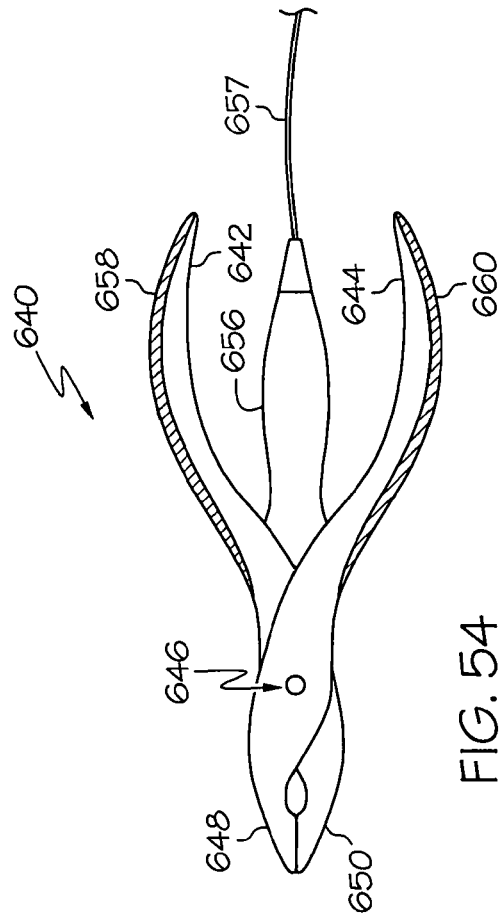
FIG. 54 illustrates one embodiment of a surgical device.
Figure 55:
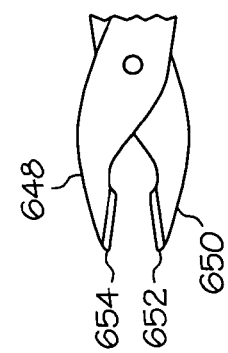
FIG. 55 illustrates a distal portion of one embodiment of the surgical device shown in FIG. 54.

FIG. 54-55 illustrate one embodiment of another force-feedback surgical device 640, which may be configured as an ultrasonic rongeur-type device. The device 640 may include a pair of handles 642, 644 that when squeezed towards one another about pivot point 646 may cause a pair of distally positioned jaw members 648, 650 to pivot towards one another to engage tissue by clamping or severing. One or both of the jaw members 648, 650 may include an ultrasonically active end effector. For example, FIG. 54 illustrates an ultrasonic end effector 652 positioned on jaw member 650 and driven by transducer 656. The transducer 656 may be in communication with a generator (not shown) via a wire 657. A clamp pad 654 may be positioned opposite the end effector 652. The transducer 656 may be positioned between the handles 642, 644, as shown, or at any other suitable position. For example, the transducer 656 may be positioned within one of the handles 642, 644. Force sensors 658, 660 may be positioned on the handles 642, 644 as shown, or may be positioned at various other locations within the device 640 including, for example, at the pivot point 646. Likewise, the control circuit (not shown) may be positioned at any suitable location on or in the device 640.

Figure 56:
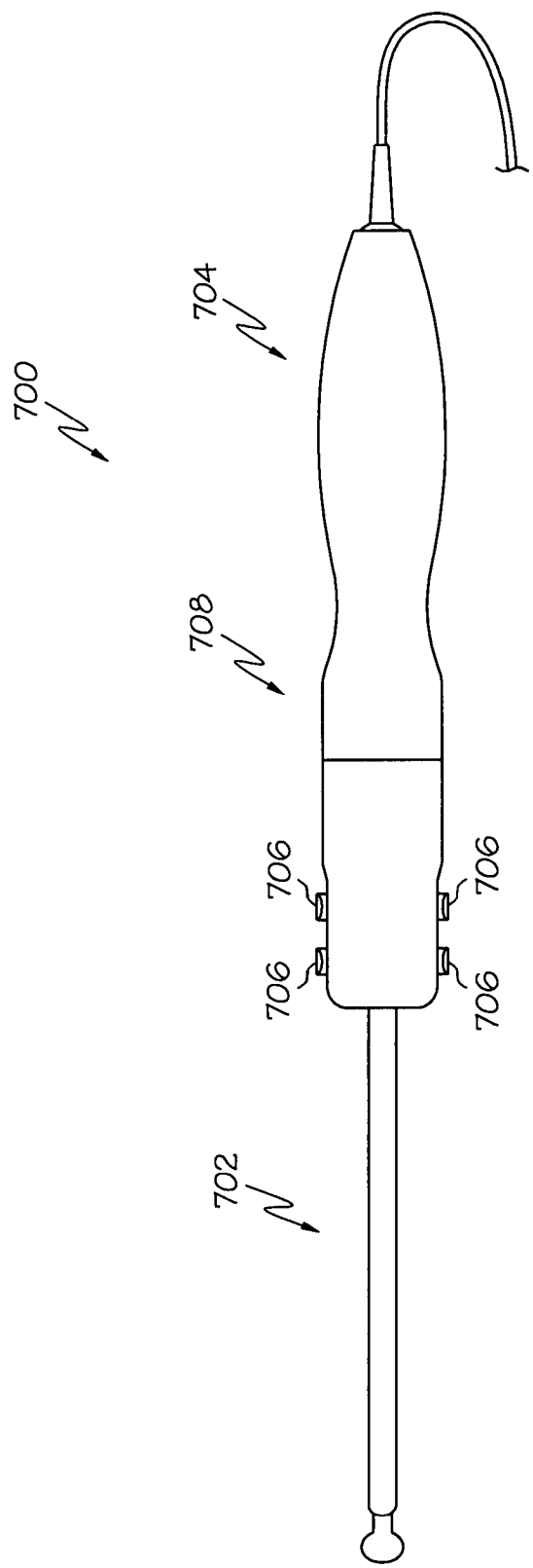
FIG. 56 illustrates one embodiment of a surgical device comprising a hand-piece adapter.

FIG. 56 illustrates one embodiment of another force feedback surgical device 700 comprising a hand-piece adapter 708. The device 700 may also comprise a transducer 704 configured to drive an end effector 702, for example, as described herein. The hand-piece adapter 708 may comprise one or more switches 706 for operating the transducer 704 and end effector 702. For example, actuating one or more of the switches 706 may cause the device 700 to activate. The switches 706 may correspond to the trigger 610 described with respect to FIG. 52. One or more sensors (not shown in FIG. 56) may be provided to sense the travel of the switches 706 and/or the amount of force applied to the switches 706 by the clinician. A control circuit (not shown in FIG. 56) may modulate the device power and/or end effector amplitude based on the output of the one or more sensors as described herein.

The devices disclosed herein can be designed to be disposed of after a single use, or they can be designed to be used multiple times. In either case, however, the device may be reconditioned for reuse after at least one use. Reconditioning can include any combination of the steps of disassembly of the device, followed by cleaning or replacement of particular elements, and subsequent reassembly. In particular, the device may be disassembled, and any number of particular elements or components of the device may be selectively replaced or removed in any combination. Upon cleaning and/or replacement of particular components, the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized prior to surgery. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical device comprising:
an end effector comprising an ultrasonic blade;
a trigger actuatable to cause the end effector to be energized;
a circuit in communication with the trigger, wherein the circuit is configured to:
when the trigger is in a first position, provide power to the end effector at a first power level; and
when the trigger is in a second position, provide power to the end effector at a second power level greater than the first power level; and
a transducer coupled to the end effector and configured to energize the end effector.

2. The surgical device of claim 1, wherein the trigger is configured to be depressed further in the second position than in the first position.

3. The surgical device of claim 2, wherein the trigger is configured to be depressed further towards a fully actuated position in the second position than in the first position.

4. The surgical device of claim 1, further comprising a ratchet device positioned to generate a sound as the trigger is moved from the first position to the second position.

5. The surgical device of claim 1, further comprising a sensor positioned to sense a position of the trigger, wherein a signal indicating a change in the position of the trigger is received from the sensor.

6. A surgical device comprising:
an end effector, the end effector comprising:
an ultrasonic blade; and
a clamp arm pivotable relative to the blade;
a transducer coupled to the blade and configured to energize the blade;
a multi-position switch actuatable to cause the blade to be energized; and
a circuit in communication with the multi-position switch and with the transducer, wherein the circuit is configured to:
when the multi-position switch is in a first position, configure the transducer to drive the end effector at a first level; and
when the multi-position switch is in a second position, configure the transducer to drive the end effector at a second level.

7. The surgical device of claim 6, wherein a power delivered to the end effector at the second level is higher than a power delivered to the end effector at the first level.

8. The surgical device of claim 6, wherein the circuit is configured to implement a delay between indicating a change in the position of a trigger mechanism and a change from driving the end effector at the first level to driving the end effector at the second level.

9. The surgical device of claim 6, further comprising a feedback device in communication with the circuit, wherein the feedback device is configured to indicate at least one of a power provided to the end effector or an amplitude of the end effector.

10. The surgical device of claim 9, wherein the feedback device comprises at least one component selected from the group consisting of:
a light source, wherein the light source indicates an amount of power delivered to the end effector by the transducer; and
a speaker, wherein the circuit is further configured to cause the speaker to emit a plurality of sounds, wherein a frequency of the plurality of sounds indicates the power delivered to the end effector.

11. The surgical device of claim 6, wherein the circuit is configured to prevent a power delivered to the end effector from exceeding a threshold power level.

12. The surgical device of claim 6, wherein the first level and the second level correspond to a first end effector amplitude and a second end effector amplitude, and wherein the second end effector amplitude is greater than the first end effector amplitude.

13. An ultrasonic surgical system for treating tissue, the system comprising:
   an ultrasonic transducer;
   an end effector comprising an ultrasonic blade coupled to the ultrasonic transducer;
   a switch having a first position and a second position; and
   a generator in communication with the switch and the ultrasonic transducer, wherein the generator is configured to:
   when the switch is in the first position, provide a first drive level to the ultrasonic transducer; and
   when the switch is in the second position, provide a second drive level to the ultrasonic transducer.

14. The system of claim 13, further comprising a feedback device in communication with the generator, wherein the feedback device is configured to indicate the first drive level when the switch is in the first position.

15. The system of claim 14, further comprising a plurality of light sources configured to illuminate to indicate the first drive level when the switch is in the first position.

16. The system of claim 14, further comprising a speaker configured to emit a plurality of sounds, wherein a frequency of the plurality of sounds indicates at least one of a power provided to the end effector or an amplitude of the end effector.

17. The system of claim 14, wherein the first drive level corresponds to a first power delivered to the end effector and the second drive level corresponds to a second power delivered to the end effector.

18. The system of claim 17, wherein the generator is further configured to prevent a power provided to the end effector from exceeding a threshold power level.

19. The system of claim 13, further comprising a handle, wherein the switch is positioned in the handle.

20. The system of claim 13, wherein the first drive level corresponds to a first end effector amplitude and the second drive level corresponds to a second end effector amplitude.

* * * * *